(12) United States Patent
Yang et al.

(10) Patent No.: US 7,146,011 B2
(45) Date of Patent: Dec. 5, 2006

(54) STEERING OF DIRECTIONAL SOUND BEAMS

(75) Inventors: Jun Yang, Singapore (SG); Woon Seng Gan, Singapore (SG); Meng Hwa Er, Singapore (SG); Chee Mun Kelvin Lee, Singapore (SG); Khim Sia Tan, Singapore (SG); Yew Hin Liew, Singapore (SG); Furi Andi Karnapi, Singapore (SG); Kan Sha, Nanjing (CN); Yi Wang, Singapore (SG)

(73) Assignee: Nanyang Technological University, Singapore (SG)

( * ) Notice: Subject to any disclaimer, the term of this patent is extended or adjusted under 35 U.S.C. 154(b) by 184 days.

(21) Appl. No.: 10/789,243

(22) Filed: Feb. 28, 2004

(65) Prior Publication Data

US 2004/0264707 A1 Dec. 30, 2004

Related U.S. Application Data

(63) Continuation of application No. PCT/SG02/00195, filed on Aug. 28, 2002.

(51) Int. Cl.
*H04B 3/00* (2006.01)
*H04B 5/00* (2006.01)
*H04B 1/02* (2006.01)
*H04R 3/00* (2006.01)
*G10S 15/00* (2006.01)

(52) U.S. Cl. .......................... 381/77; 381/79; 381/111; 381/116; 367/92; 367/138

(58) Field of Classification Search ............ 381/77, 381/79, 111, 116; 367/92, 138
See application file for complete search history.

(56) References Cited

U.S. PATENT DOCUMENTS 5,081,995 A * 1/1992 Lu et al. ..................... 600/459

(Continued)

FOREIGN PATENT DOCUMENTS

DE 2841680 A 4/1980

(Continued)

OTHER PUBLICATIONS

International Preliminary Examination Report dated Jan. 16, 2004 in corresponding international application PCT/SG02/00195.

(Continued)

*Primary Examiner*—Vivian Chin
*Assistant Examiner*—Devona E. Faulk
(74) *Attorney, Agent, or Firm*—Rissman Jobse Hendricks & Oliverio, LLP

(57) ABSTRACT

Apparatus is disclosed for steering a directional audio beam that is self-demodulated from an ultrasound carrier. The apparatus includes means for modulating a carrier signal with an audio signal and means for adjusting the amplitude and phase of at least one of the audio signal and/or the carrier signal to steer the audio beam to a desired direction. The apparatus also includes means for generating an ultrasound beam in the desired direction driven by the modulated carrier signal. The apparatus may include means for weighting the audio and/or carrier signal by a zeroth order Bessel function to synthesize a Bessel distribution source. A corresponding method for steering a directional audio beam is also disclosed. A harmonic generator may be used to generate harmonics of low frequencies in the audio signal. The harmonics may provide (upon demodulation) a psycho-acoustic impression of improved perception of low frequencies. Further, a modulated ultrasonic signal or an unmodulated audio signal may be band-passed into two or more different band-limited signals. The band-limited signals may be amplified and transmitted by ultrasonic transducers having mechanical resonance frequencies substantially equal to a characteristic frequency of the band-limited signals. Ultrasonic processing of the audio signal may include square root methods without generating large numbers of harmonics.

11 Claims, 18 Drawing Sheets

U.S. PATENT DOCUMENTS

| | | | |
|---|---|---|---|
| 5,341,167 A | 8/1994 | Guichard | 348/14 |
| 5,718,227 A | 2/1998 | Witlin | 128/660.02 |
| 5,740,804 A * | 4/1998 | Cerofolini | 600/459 |
| 5,911,692 A * | 6/1999 | Hussain et al. | 600/447 |
| 6,052,336 A | 4/2000 | Korolenko | 367/121 |

FOREIGN PATENT DOCUMENTS

| | | | |
|---|---|---|---|
| EP | 973152 A2 * | 1/2000 | |
| EP | 0973152 A2 | 1/2000 | |
| GB | 2121174 | 12/1983 | |
| WO | WO 98/02976 | 1/1998 | |
| WO | WO 98/49868 | 11/1998 | |
| WO | WO 01/52437 | 7/2001 | |

OTHER PUBLICATIONS

International Search Report dated Dec. 4, 2002 in corresponding international application PCT/SG02/00195.

* cited by examiner

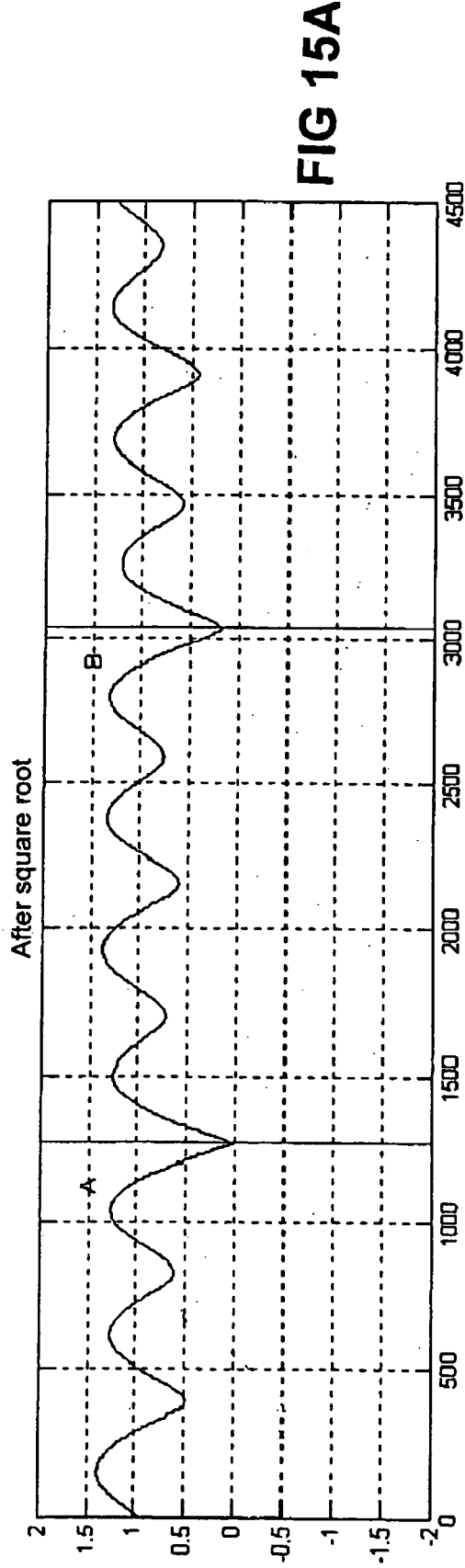
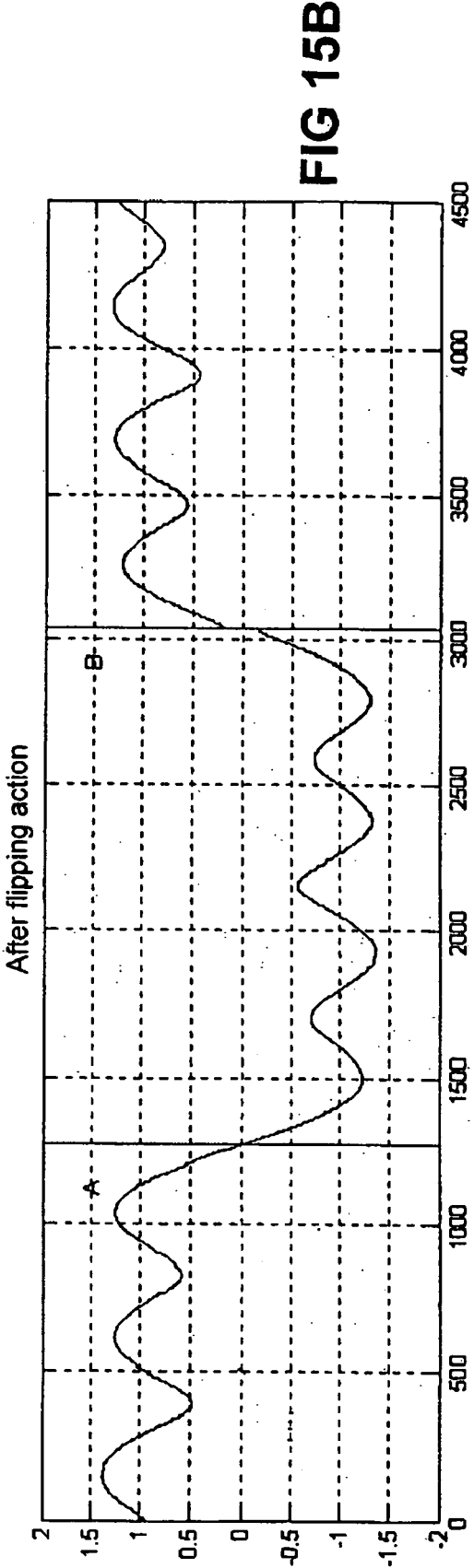

STEERING OF DIRECTIONAL SOUND BEAMS

RELATED APPLICATIONS

This application is a continuation of and claims priority under 35 USC § 119, 120 and/or 365 to PCT patent application No. PCT/SG02/00195, filed Aug. 28, 2002, which claimed priority of Singapore Patent Application No. 200200437-2, filed Jan. 25, 2002, Singapore Patent Application No. 200105345-3 filed Aug. 31, 2001 and Singapore Patent Application No. 200105344-6, filed Aug. 31, 2001.

FIELD OF THE INVENTION

The present invention relates to the field of ultrasonics and nonlinear acoustics for generating hyper-directional audible sound beams. In particular the invention relates to a method and apparatus for steering the hyper-directional sound beams to a desired location and to systems incorporating such method and apparatus. The present invention also presents preprocessing methods for reducing distortion and enhancing perception of bass frequencies, as well as techniques for reducing bandwidth requirements in associated ultrasonic transducers.

BACKGROUND OF THE INVENTION

An audio system for generating hyper-directional sound beams in the audible range is known. The audio system employs an array of acoustic transducers to project through the air an ultrasonic carrier wave modulated with signals representing audible sounds. Due to non-linear propagation characteristics of transmission media such as air when excited by finite amplitude ultrasonic waves, the modulated ultrasound self demodulates on passage through the transmission medium, creating endfire virtual sources along a selected projection path to produce a hyper-directional sound beam in the audible range. Although the sound beam is demodulated with relatively high levels of harmonic and intermodulation distortions it is possible to obtain a relatively linearized characteristic by pre-distorting or pre-conditioning the audible signal before modulation.

In particular, it is noted that, when the primary wave is a modulated carrier, the sound generated (upon demodulation) by the secondary (modulating) wave is proportional to the second time derivative of the square of the modulation envelope. This results in high levels of harmonic distortion in the sound generated. To address this, D. T. Blackstock (refer "Audio Application of the Parametric Array," J. Acoust. Soc. Am., Vol 102 pp 3106(A), 1997) and others (refer T. Kamakura, M. Yoneyama, K. Ikegaya, "Developments of parametric loudspeaker for practical use", $10^{th}$ Int. Symp. Nonlin. Acous., pp. 147–150, 1984 and T. D. Kite, J. T. Post and M. F. Hamilton, "Parametric array in air: distortion reduction by preprocessing", Proc. Int. Conf. Acous./Acous. Soc. Am, vol. 2, pp. 1091–1092, June 1998.) suggest methods of improving distortion in the demodulated signal. Blackstock proposes integrating the original signal twice and taking the square root thereof; to anticipate the demodulation function and thus remove the distortion resulting from demodulation. This is shown in the following equation, where f(t) is the audio signal and E(t) is the signal provided to the modulator:

$$E(t) = (1 + \int \int f(t) dt^2)^{1/2} \quad (1)$$

However, due to the square root operation, this preprocessing approach generates an infinite number of harmonics. Harmonic distortion will only be removed if all of these harmonics are reproduced. Therefore, the amount of distortion of the demodulated signal is directly related to the bandwidth of the device, and the method requires bandwidth-intensive ultrasonic paths and emitters to get optimal performance.

The sound beams produced by the above technique may be focused, steered or projected in a defined area or direction. Reflection may take place when the modulated carrier wave encounters an object that absorbs energy at ultrasonic frequencies but reflects energy at audio frequencies.

Advantages of using an ultrasonic carrier wave to deliver audio include the highly directional nature of the modulated ultrasonic wave, the fact that the carrier wave is steerable (for example by providing reflective surfaces), and also that the signal is not audible prior to demodulation. By proper application of these advantages, audio can be delivered to specific locations, from where the audio appears to originate. A general discussion of the transmission of audio signals can be found in European published patent application no. EP 973 152.

However, other technical challenges remain in the use of ultrasonic technology for delivering audio. For example, the fidelity of the demodulated audio signal can still be improved. In particular, the delivery of adequate power at low frequencies is a problem. Human hearing is more sensitive to stimuli having middle frequency components (i.e. 3–4 kHz) than low frequency components (i.e. "bass," below 500 Hz). To perceive lower frequency sounds at the same loudness as at the middle frequencies, it is necessary to generate higher sound pressure levels at the lower frequency.

One useful application for the sound beams is in advertising. A problem with simultaneous audio-broadcasting of advertising material is that it creates noise pollution in public places such as shopping malls, public transport stations (bus stops and train terminals), conference and exhibition halls and the like. This may create a relatively high level of interference and confusion for the listener who hears mixed signals from different broadcasting sources.

A parametric audio system incorporating a steering function that uses a phased array technique is described in WO01/52437 (Frank Joseph Pompei). The latter system includes a delay circuit to apply a relative phase shift or delay across all frequencies of the modulated carrier signal to steer, focus, or shape ultrasonic beams generated by the acoustic transducer array.

SUMMARY OF THE INVENTION

The present invention may address this problem by creating a private listening space for passers-by, passengers, shoppers and visitors without contributing significantly to noise pollution of the environment. At the same instant, a more coherent and intelligible message may reach the listener without experiencing too much distortion and noise interference. A variation of the present invention may provide a directional audio directory which can act as a guide for directing passers-by to their destinations. The present invention may allow conventional billboards each incorporating a sound beam to be placed relatively close to one another and still be able to maintain their respective private listening spaces without mutual interference.

The sound beam may be steered by mechanical means such as a stepper motor which may be arranged to rotate the array of transducers to cover an immediate area in front of a billboard panel, for example. An alternative may make use of digital beamforming techniques to perform a similar function.

The array of transducers may directly project at the listener or alternatively may project at a surface which serves to reflect the directional sound to the listener. The latter may create an audible image of the sound source and the impression on the listener that the sound is transmitted directly from the surface.

An extension to the present invention may include a video camera to provide an image of a potential listener. An intelligent tracking system may detect the location of the listener and may steer the sound beam directly to the listener to allow a message to follow a moving listener.

The present invention may create a private listening space around the listener without disturbing his neighbors. The system of the present invention may accept an audio signal from any one of a plurality of sources including a CD player, FM radio receiver or digital broadcast radio receiver and transmit it within the area of the private listening space.

Moreover, if traditional lead zirconate titanate (PZT) transducers are adopted, each device may have a slightly different peak frequency or there may be a slightly different phase corresponding to each resonant frequency. To ensure uniform transducers, matching filters may be introduced, e.g. by electrically controlling delay to each transducer.

The present invention may provide a beamforming technique which may suitably adjust not only the phases of the primary waves, notably both the modulating signal in the audible range and the carrier signal in the ultrasonic range as discussed previously, but may also adjust the amplitudes or weights of the transducer elements in the parametric array to steer the sound beam. Such weight adjustments can be used to minimize spreading of the sound beam over large distances by the use of a Bessel distribution source. The latter may be constructed by weighting the arrangement of transducers by a Bessel function to produce a non-diffracting beam. The transducers may be driven with amplitudes which are adjusted to produce a zeroth order Bessel function. In theory such a beam travels to infinity without spreading. This may reduce the requirement of power and ensure high directivity along a desired path over a large distance. The transducers may be arranged in an annular or substantially annular array.

Use of an ultrasonic wave having a pressure profile that approximates a zeroth order Bessel function to minimize diffraction of the wave is described in U.S. Pat. No. 5,081, 995 (Mayo foundation for Medical Education and Research). The theory for designing non-diffracting ultrasound beam is given by J. Durnin in an article "Exact solutions for non-diffracting beams. I. The scalar theory." published in the *Journal of Optical Society of America* 4(4): 651–654, 1987. This solution indicates that transducers can be constructed which produce a wave that is confined to a beam that does not diffract, or spread, over a long distance. The disclosures of the two latter documents are incorporated herein by cross reference.

An alternative to a zeroth order Bessel weight function may be to suppress a sidelobe of the steered beam pattern. Examples of alternative weight functions may include:

1. Chebyshev window with different values of relative sidelobe attenuation (decibels).
2. Hamming window
3. Hanning window
4. Blackman window and other weight functions/windows that may be used to suppress the sidelobe of the steered beam.

A harmonic generator may be used to generate harmonics of relatively low frequencies in an audio signal. These harmonics and the audio signal may then be modulated onto an ultrasonic carrier wave and transmitted by ultrasonic emitters to provide (upon demodulation) a psycho-acoustic impression of improved perception at low frequencies. The harmonics may be combined with the original or otherwise-modified audio signal prior to modulation and transmission, or it may be modulated and/or transmitted separately but simultaneously.

The modulated ultrasonic signal may be band-passed into two or more different band-limited signals with overlapping/non-overlapping frequency bands at center frequencies of $f_1$ to $f_N$ respectively. The band-limited signals may be amplified and transmitted by different ultrasonic transducers (or groups of ultrasonic transducers) having mechanical resonance frequencies substantially equal to a characteristic frequency Of the band limited signal. Typically, the mechanical resonance frequencies are substantially equal to the center resonant frequencies $f_1$ to $f_N$.

The unmodulated audio signal may be bandpassed into two or more different band-limited signals with overlapping/non-overlapping frequency bands. These band-limited signals may be provided to separate ultrasonic modulators that have the same or different carrier frequencies. The resulting modulated signals may be provided to ultrasonic emitters that have mechanical resonant frequencies substantially equal to a characteristic frequency of the modulated signals.

According to one aspect of the present invention there is provided an apparatus for steering a directional audio beam that is self-demodulated from an ultrasound carrier, said apparatus including:

means for generating an audio signal;

means for generating an ultrasound carrier signal;

means for modulating said carrier signal with said audio signal;

means for adjusting the amplitude and phase of at least one of said audio signal and said carrier signal to steer said audio beam to a desired direction; and means for generating an ultrasound beam in said direction driven by said modulated carrier signal.

According to a further aspect of the present invention there is provided an apparatus for steering a directional audio beam that is self-demodulated from an ultrasound carrier, said apparatus including:

means for generating an audio signal;

means for generating an ultrasound carrier signal;

means for modulating said carrier signal with said audio signal;

means for generating an ultrasound beam driven by said modulated carrier signal; and means for adjusting said means for generating to steer said audio beam to a desired location.

According to a still further aspect of the present invention there is provided a method of steering a directional audio beam that is self-demodulated from an ultrasound carrier, said method including the steps of:

generating an audio signal;

generating an ultrasound carrier signal;

modulating said carrier signal with said audio signal;

adjusting the amplitude and phase of at least one of said audio signal and said carrier signal to steer said audio beam to a desired direction; and generating an ultrasound beam in said direction driven by said modulated carrier signal.

According to a still further aspect of the present invention there is provided a method for steering a directional audio beam that is self-demodulated from an ultrasound carrier, said method including the steps of:

generating an audio signal;

generating an ultrasound carrier signal;

modulating said carrier signal with said audio signal;

generating an ultrasound beam driven by said modulated carrier signal; and adjusting said means for generating to steer said audio beam to a desired direction.

According to a still further aspect of the present invention there is provided a method of processing an audio signal, including:

performing a square root operation on the audio signal to generate a square rooted signal;

alternating the gain of the square rooted signal between positive and negative gain values at selected locations to generate a flipped signal; and modulating the flipped signal onto a first ultrasonic carrier wave.

Preferably the audio signal is offset by a predetermined amount prior to performing the square root operation to ensure that the square root operation results in real values only.

The method also preferably includes:

dividing the audio signal into a plurality of frames;

determining, after the offsetting step, a minimum value of a portion of the audio signal in a particular frame; and subtracting the minimum value from the portion of the audio signal in the particular frame.

In a preferred embodiment, the selected locations between which the signal is flipped may be minimum turning points of the signal.

The method may include the steps of:

determining a first modulation envelope for the flipped signal;

determining a second modulation envelope for the square rooted signal;

determining the difference between the first and second modulation envelopes;

modulating the difference between the first and second modulation envelopes onto a second ultrasonic carrier wave.

The first and second ultrasonic carrier waves may be orthogonal to one another.

According to a still further aspect of the present invention, there is provided an apparatus for processing an audio signal received from an audio source including:

a square root module to perform a square root operation on the audio signal to generate a square rooted signal;

a determining module coupled to the square root module to alternate the gain of the square rooted signal between positive and negative gain values at selected locations thereby to generate a flipped signal; and a modulator to modulate the flipped signal onto a first ultrasonic carrier wave.

The apparatus may further include:

an offset module to offset the audio signal by a predetermined amount prior to passing the signal to the square root module.

The apparatus may also include:

a buffer to divide the audio signal into a plurality of frames;

a subtracting module to subtract a minimum value from the portion of the audio signal in the particular frame.

Preferably, the determining module may also determine a first modulation envelope for the flipped signal;

determine a second modulation envelope for the square rooted signal;

determine the difference between the first and second modulation envelopes; and the modulator modulates the difference between the first and second modulation envelopes onto a second ultrasonic carrier wave.

According to a still further aspect of the present invention, there is provided a method for processing an audio signal received from an audio source, including:

processing the audio signal into a first processed audio signal;

processing the audio signal into a second processed audio signal;

modulating the first processed audio signal onto a first ultrasonic carrier wave; and modulating the second processed audio signal onto a second ultrasonic carrier wave; wherein the first and second ultrasonic carrier waves have different phases.

The first ultrasonic carrier wave may be orthogonal to the second ultrasonic carrier wave.

According to a still further aspect of the present invention there is provided an apparatus for processing an audio signal received from an audio source, including:

a processor to process the audio signal into a first processed audio signal and a second processed audio signal;

a modulator to modulate the first processed audio signal onto a first ultrasonic carrier wave and to modulate the second processed audio signal onto a second ultrasonic carrier wave;

wherein the first and second ultrasonic carrier waves have different phases.

The first ultrasonic carrier wave may be orthogonal to the second ultrasonic carrier wave.

According to a still further aspect of the present invention there is provided a method of processing an audio signal, including:

separating a low frequency component from the audio signal;

generating harmonics of the low frequency signal to create a preprocessed signal; and modulating the preprocessed signal onto an ultrasonic carrier wave.

According to a still further aspect of the present invention there is provided a method of processing an audio signal including the steps of:

separating the audio signal into a plurality of band-limited signals;

modulating each of the band-limited signals onto ultrasonic carrier waves having either the same or different carrier frequencies thereby to create a plurality of modulated signals; and transmitting each of the modulated signals from separate ultrasonic emitters.

According to a still further aspect of the present invention there is provided a method of processing an audio signal including the steps of:

modulating the audio signal onto an ultrasonic carrier wave to provide a modulated audio signal;

separating the modulated audio signal into a plurality of band-limited signals; and transmitting each of the plurality of frequency bands from a separate ultrasonic transmitter.

According to a still further aspect of the present invention there is provided an apparatus for processing an audio signal received from an audio source, including:

a first filter to separate a low frequency component from the audio signal;

a harmonies generator to generate harmonics of the low frequency component; and an ultrasonic modulator to modulate the low frequency component and the harmonics onto an ultrasonic carrier wave.

According to a still further aspect of the present invention there is provided an apparatus for processing an audio signal including:

a filter bank for separating the audio signal into a plurality of band-limited signals;

a plurality of ultrasonic modulators corresponding to the respective band-limited signals to modulate each of the band-limited signals onto an ultrasonic carrier wave; and a plurality of ultrasonic emitters for receiving and transmitting the modulated band-limited signals.

According to a still further aspect of the present invention there is provided an apparatus for processing an audio signal, including:

an ultrasonic modulator to modulate the audio signal onto an ultrasonic carrier wave thereby to create a modulated audio signal;

a filter bank to separate the modulated audio signal into a plurality of band-limited signals. Preferably the apparatus includes a plurality of ultrasonic emitters to transmit the plurality of band-limited signals.

BRIEF DESCRIPTION OF THE DRAWINGS

Preferred embodiments of the present invention will now be described with reference to the accompanying drawings wherein:—

FIG. 1 shows an audio billboard that beams directional audio to passers by;

FIGS. 15A and 15B shows two curves illustrating processing performed in the system of FIGS. 13 and 14;

DETAILED DESCRIPTION

Figure 1:
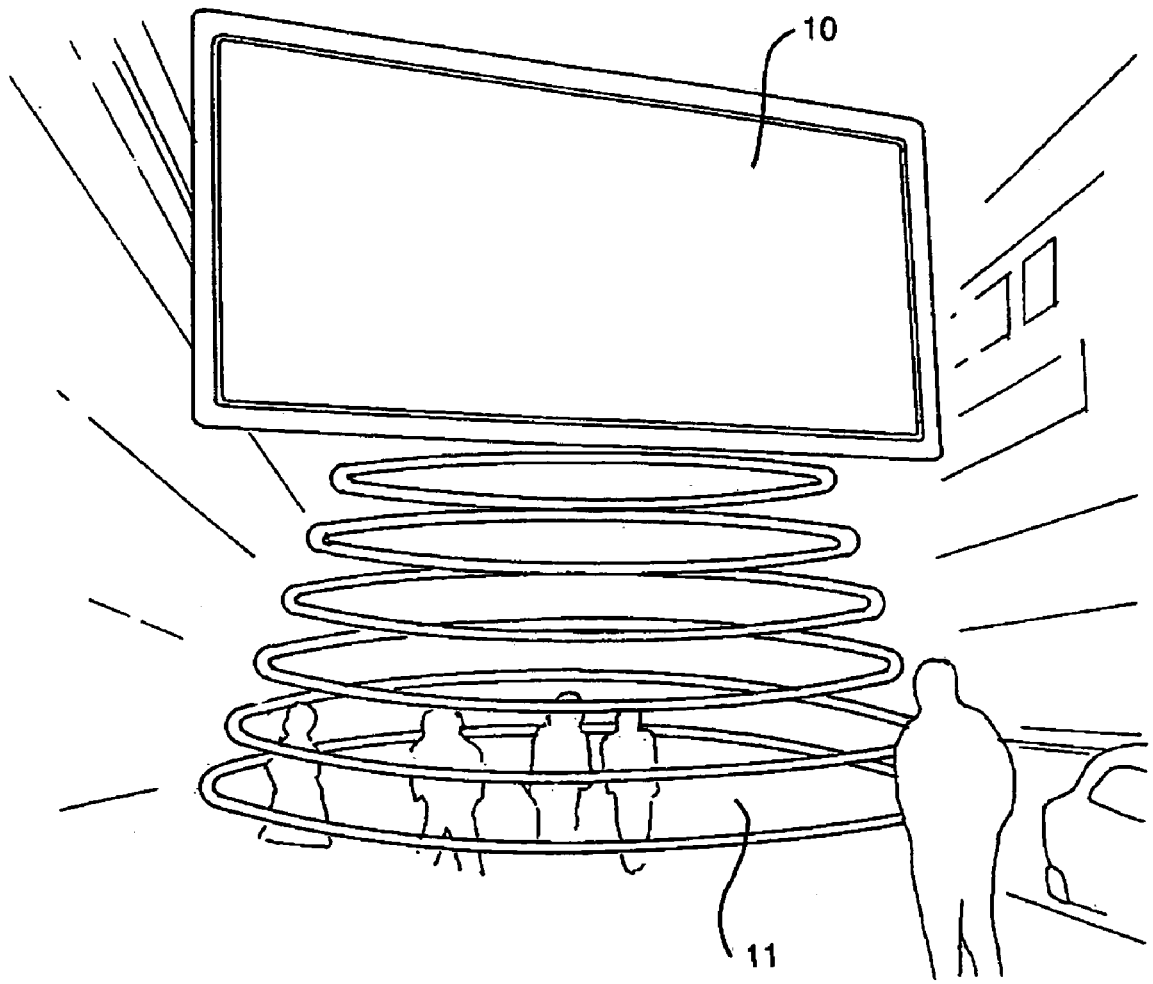

FIG. 1 shows billboard panel 10 which incorporates a system for generating a hyper-directional audible sound beam 11 according to the present invention. The billboard encompasses an implementation and integration of an array of ultrasonic transducers which generates the directional sound beam in association with a conventional billboard panel. The system may include a digital signal processing module that processes an audio signal from a sound source and sends it to a modulating and amplifying circuit. This in turn drives a group of ultrasonic transducers in the array and transmits a modulated ultrasonic beam. At high sound pressure levels, self-demodulation occurs due to nonlinear interaction in air and causes secondary audible frequencies to appear within the beam. Such a phenomenon of creating new sounds or virtual sources along a selected projection path (such that they reinforce one another) enables a hyper-directional sound beam to be produced in the audible range. These newly produced secondary waves in the air retain the narrow beam characteristics of the primary counterpart and are useful in creating a private listening or advertising space around the listener. Sound sources into the signal processing module may be provided from a CD player, FM radio receiver or a digital broadcast radio receiver.

Figure 2:
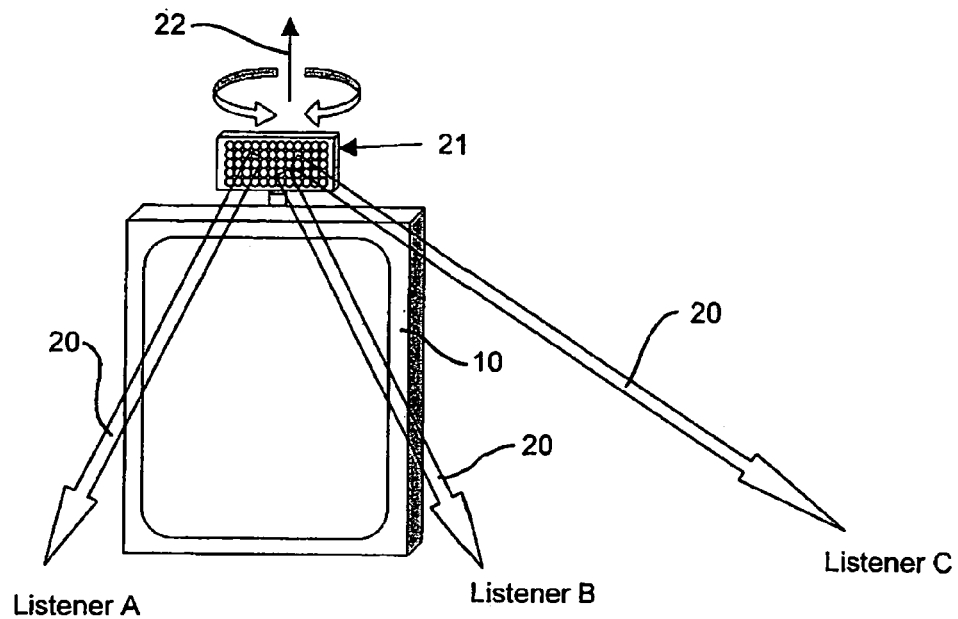
FIG. 2 shows one arrangement of audio transducers associated with a billboard.

FIG. 2 shows an arrangement for steering the sound beam 20 to a specified area or location. The arrangement may include a stepper motor (not shown) for rotating an array of ultrasonic transducers 21 at least relative to vertical axis 22. The stepper motor may be installed at the base of array 21 to enable array 21 to be rotated to allow beam 20 to cover an immediate area in front of billboard panel 10 to reach listener A, B or C selectively. The beam 20 may produce a private advertising space in the vicinity of the selected listener which does not intrude on adjacent spaces. A digital beam steering device as described below may be used in place of the stepper motor to perform a similar function.

An alternative placement for ultrasonic transducer array 21 is in a housing directly behind the billboard panel 10. Panel 10 may include a graphic poster made of permeable fabric or other suitable or porous medium. The audio beam propagating out of the array may penetrate through the porous medium without significant signal attenuation and there is less space consumption since transducer array 21 is concealed behind the poster inside the housing of panel 10.

A further extension may include a video camera to provide an image of the potential listener. An intelligent tracking system may detect the location of the listener and may steer the audio beam directly to the listener to allow a message to follow a moving listener or passenger. The array of transducers can be arranged in a convex shape to widen the arc of the beam.

Figure 3:
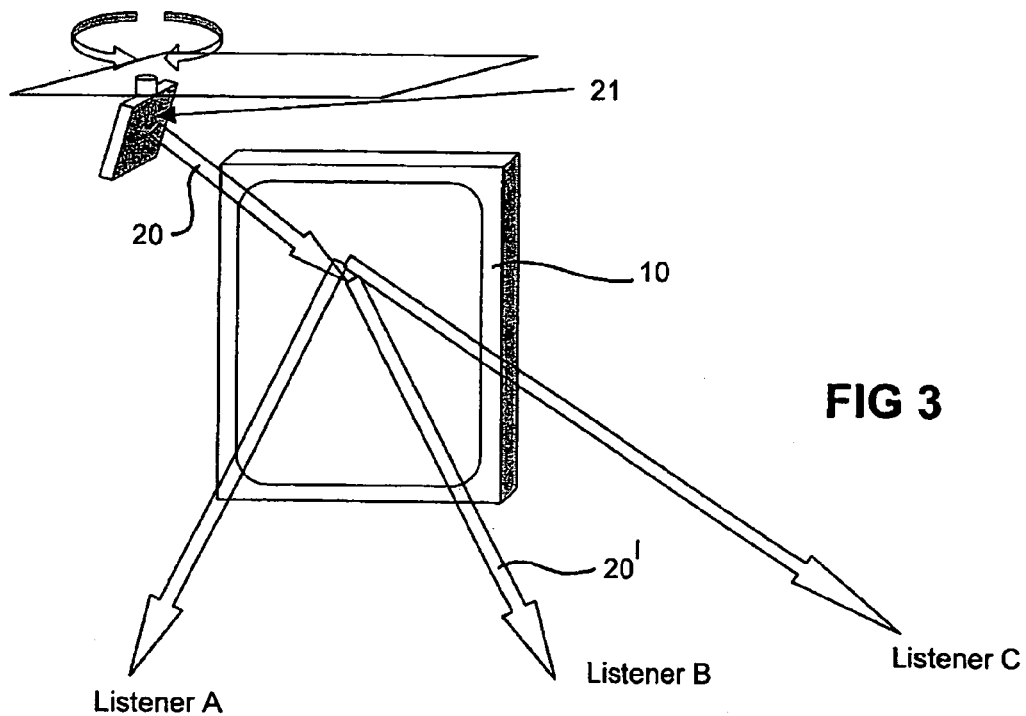
FIG. 3 shows an alternative arrangement of audio transducers associated with a billboard.

FIG. 3 shows an arrangement similar to FIG. 2 in which the sound beam 20 is reflected from the surface of billboard panel 10 to reach a listener as a reflected beam 20' to produce the impression of a sound source emanating from the surface of billboard panel 10.

Figure 4:
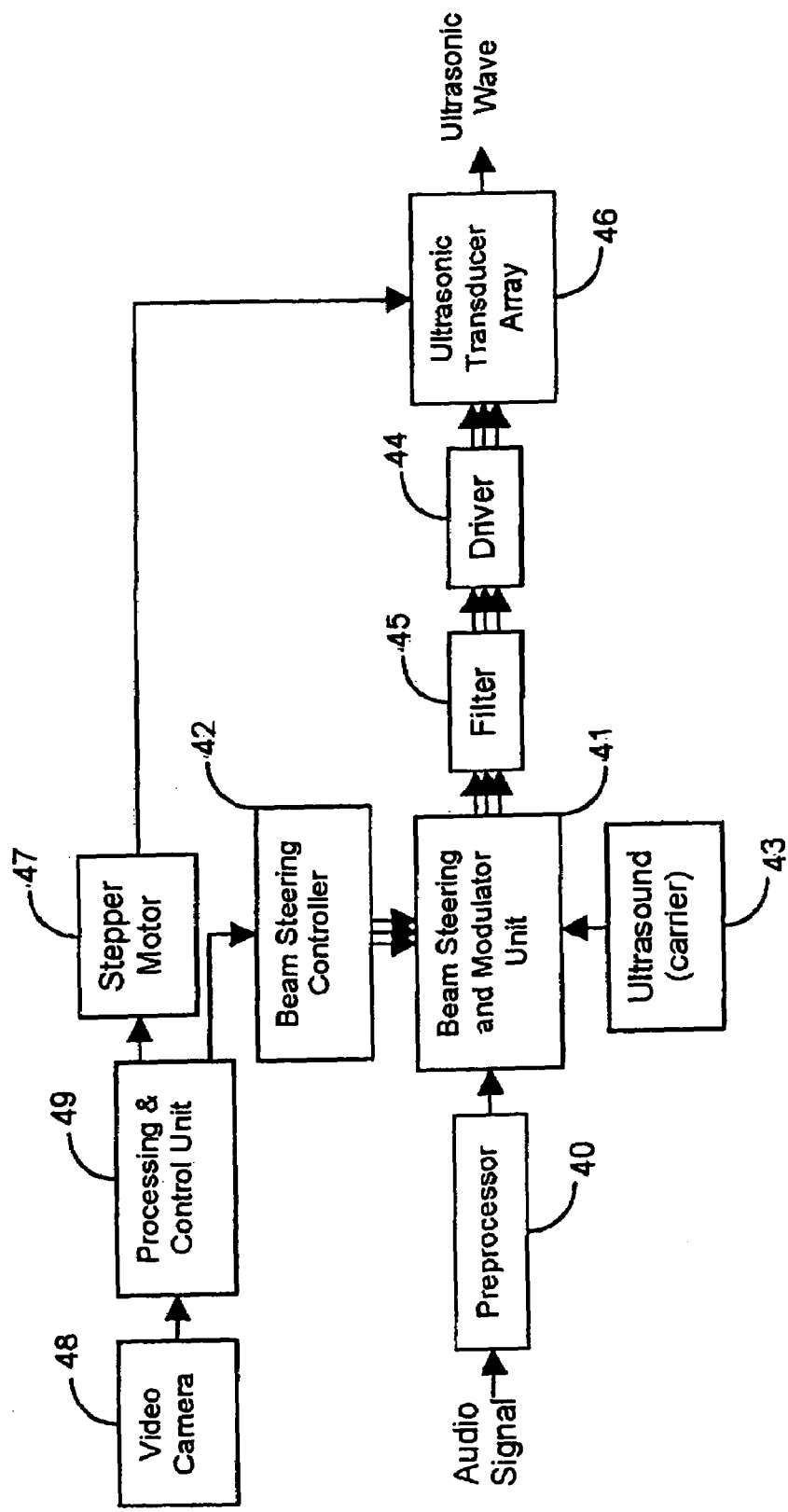
FIG. 4 is a schematic diagram of control and processing apparatus associated with an audio billboard according to the present invention.
Figure 5:
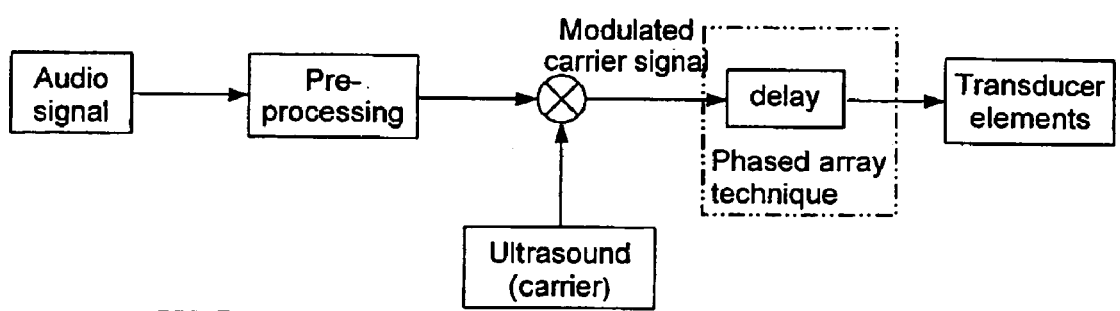
FIG. 5 shows a prior art phased array technique.

The apparatus shown in FIG. 4 includes preprocessor module 40 for processing an audio signal from a sound source such as a CD player, FM radio or digital broadcast radio receiver. In preprocessor module 40, a DC offset is first applied to the audio signal in such a way as to enhance the audio quality of the resultant demodulated signal. The preprocessor may include means to predistort or precondition the signal in order to obtain a relatively linearized characteristic after self demodulation of the audio signal. One form of preprocessing is discussed in a paper entitled Parametric Array in Air: Distortion Reduction by Preprocessing by Thomas D. Kite, et al., ICA/ASA Proceedings, Seattle Wash. June 1998. Another form of preprocessing or equalization is discussed in a paper entitled The audio spotlight: An application of nonlinear interaction of sound waves to a new type of loudspeaker design by Masahide Yoneyama et al. J. Acoustical Society of America Vol. 73 No. 5 May 1983. The disclosures of the two later documents are incorporated herein by cross reference.

The output from preprocessor module 40 is sent to beam steering and modulator unit 41. Beam steering and modulator unit 41 will accept a control signal from beam steering controller 42 and performs gain and delay adjustment for beamforming (non-diffraction Bessel-type) and beam steering. In addition, beam steering and modulator unit 41 receives ultrasound carrier 43 and modulates the signal from preprocessor module 40 to an ultrasonic signal and sends it to driver 44 via filter module 45. The modulated ultrasonic signal is amplified via driver 44 sufficiently to drive an array of ultrasonic transducers 46 (also known as a parametric acoustic array) to produce a finite-amplitude (high pressure level) modulated ultrasonic beam.

Because practical transducers have slightly different peak frequencies which limit their arrayability, a corresponding set of matching filters is included in filter module 45 for aligning the transducers. The matching filters in module 45 individually control the delay to each transducer to adjust the phase of the driving signal to the resonant frequency of the associated transducer. Phase alignment of array 46 provides a more effective radiation pattern that is not distorted as a result of variations in transducer response characteristics.

To steer the beam to a specified area or direction, stepper motor 47 is installed at the base of the ultrasonic transducer array 46 to enable the device to be rotated and to cover the immediate area in front of a billboard panel. A digital beam steering controller 42 as described herein may also be incorporated into the ultrasonic transducer array to perform a similar function or to extend the range of steering of the beam. The transducer array 46 can be used to directly project at the listener or to project at a surface which serves to reflect the directional sound to the listener as described with reference to FIG. 3. The latter may create an image of the sound source and the impression on the listener that the same sound is transmitted directly from the surface.

Video camera 48 may provide an image of a target zone in the vicinity of a billboard in which potential listeners or the sound beams may move. Image processing and control unit 49 may include an image recognition capability to detect moving listeners in the target zone and to control stepper motor 47 and/or beam steering controller unit 41 to steer ultrasonic transducer array 46 towards and with the moving listeners.

In FIG. 4, there are several means of controlling the direction of the beam, which make use of beam steering controller unit 41 and/or stepper motor 47. For example, if stepper motor 47 only is used, it may rotate ultrasonic transducer array 46 to the desired direction (i.e. beam steering controller 42 is not used to control the direction of the beam). Alternatively, beam steering controller 42 may be used in place of stepper motor 47 (i.e. stepper motor 47 is not used to control the direction of the beam). Finally, beam steering controller 42 and stepper motor 47 may be used in combination. This may provide a wider range of directions and a more flexible manner of controlling the beam.

Figure 6:
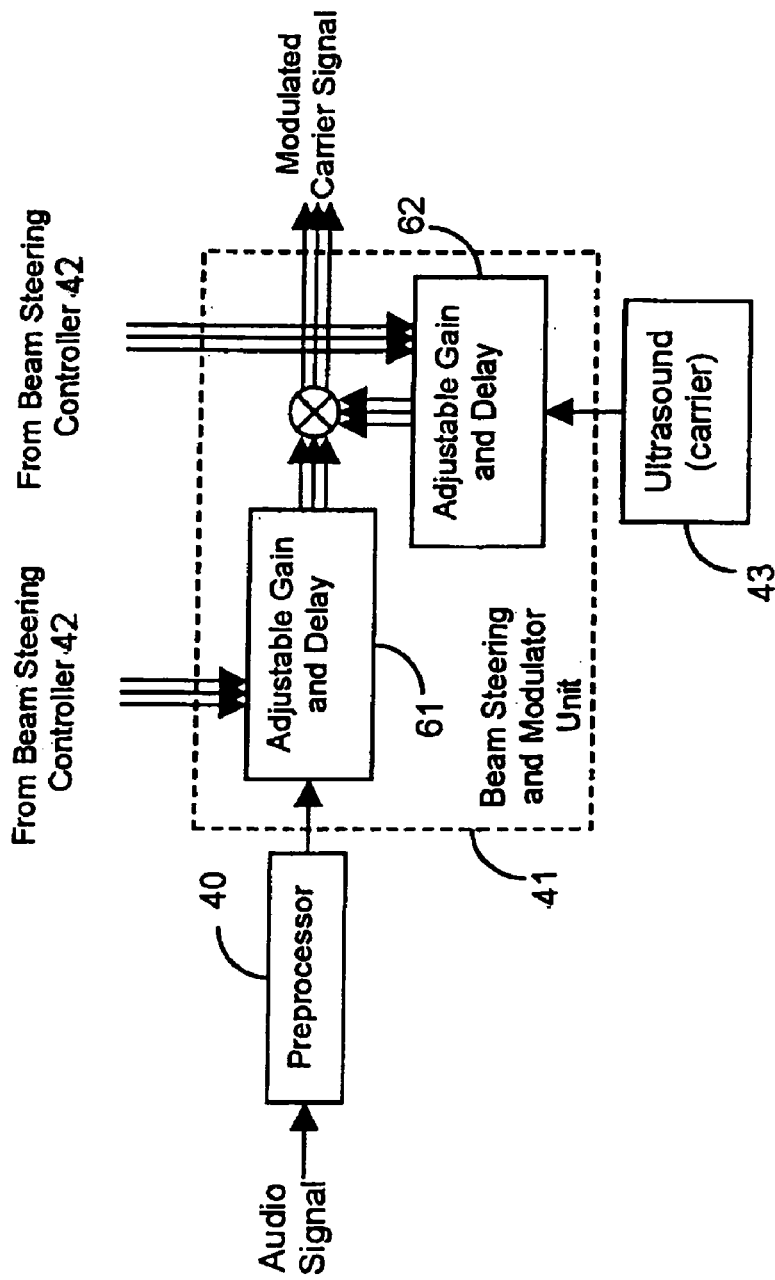
FIG. 6 is a schematic diagram of an ultrasound modulator incorporating beam steering according to the present invention.

FIG. 6 is a schematic diagram of a beam steering arrangement according to the present invention. The beam steering arrangement includes beam steering unit 41 receiving a pre-processed audio signal from preprocessor module 40. Preprocessor module 40 applies a pre-distorting or equalizing function to the audio signal as described above to obtain a relatively linearized characteristic for the demodulated sound beam. Beam steering unit 41 includes gain and phase adjustment modules 61, 62 for adjusting the amplitude and phase of the pre-conditioned audio signal and ultrasound carrier 43 respectively. Beam steering controller 42 is used to deliver gain and phase information to beam steering unit 41. The modulated carrier signal is applied to driver 44 which drives ultrasonic transducer array 46 as described with reference to FIG. 4.

Figure 7:
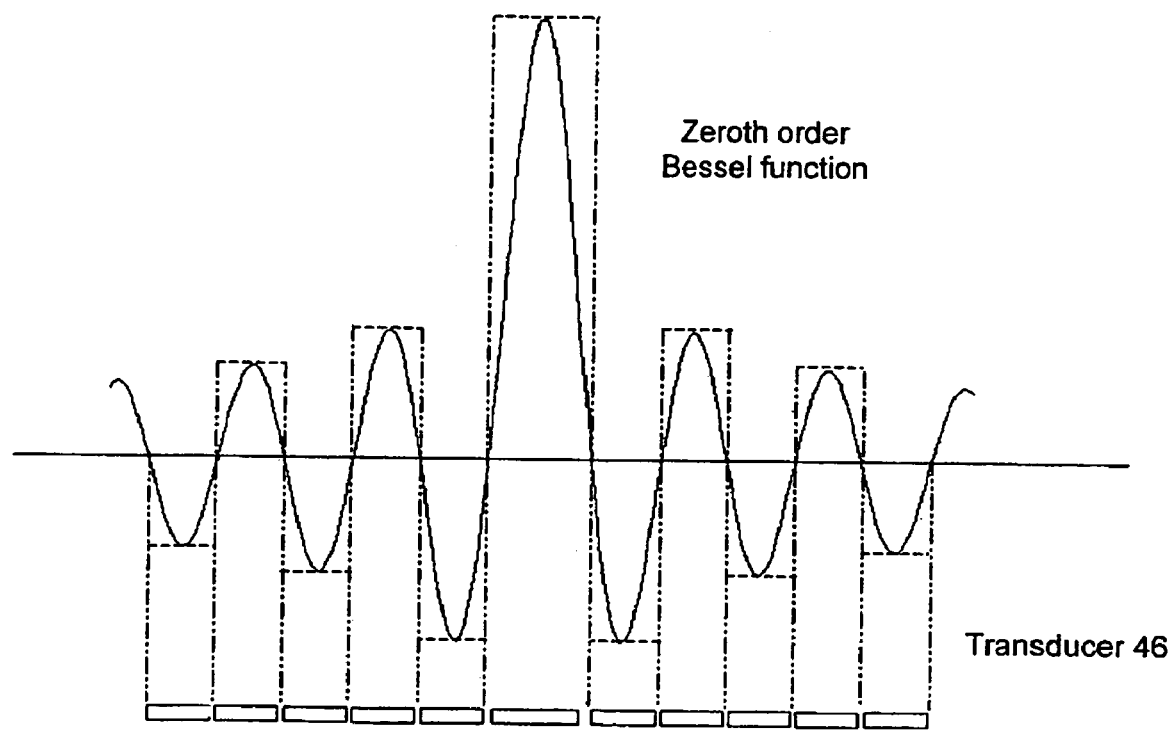
FIG. 7 shows a graphical representation of the profile of a zeroth order Bessel function and an associated ultrasound pressure profile produced by an ultrasonic transducer.

To obtain a substantially diffraction-free radiation pattern the array is weighted by a Bessel function to construct a Bessel distribution source (see FIG. 7). The Bessel function is implemented via either or both Bessel beam generators included in modules 61 and 62 that receive a suitable vector of gains and delays from beam steering controller 42. The Bessel beam generators include a plurality of adjustable gains, each of which corresponds to a respective transducer element. While the delays are applied in the said methods to steer the audible sound beam, the gains are adapted to synthesize a zeroth order Bessel function along a desired steering path or direction. In the preferred embodiment, an exact solution of the wave equation for free space, $$\left(\nabla^2 - \frac{1}{c^2}\frac{\partial^2}{\partial t^2}\right)\psi(\vec{r},t) = 0 \qquad (2)$$

is given by $$\psi(\vec{r},t) = e^{-j\omega t}\int_0^{2\pi} \exp\{i\alpha[x\cos(\phi)+y\sin(\phi)] + i\beta z\}d\phi \qquad (3)$$

where $\nabla^2 = \partial^2/\partial r^2 + (1/r)\partial/\partial r$ is the Laplacian operator, $\phi$ is the polar angle, $\vec{r}$ represents the observing point, t is time, $\omega$ is angular frequency of the sound, and c is the speed of sound. Denoting $\theta$ to be the angle that wave vector makes with the z axis, gives $$\alpha = k\cos(\theta) \qquad (4)$$

and $$\beta = k\sin(\theta) \qquad (5)$$

Physically, the integral in Eq. (3) represents plane waves propagating at a fixed angle $\theta$ with respect to the z axis for all $2\pi$ polar angles, and can be shown to be proportional to the zeroth-order Bessel function, $J_0$, giving a field $\psi(\vec{r},t)$ of $$\psi(\vec{r},t) = e^{i(\beta z - \omega t)} \cdot J_0(\alpha r) \qquad (6)$$

when $0 < \alpha \leq k$, this beam being non-diffracting.

The array of transducers may be arranged in an annular array to facilitate synthesis of a zeroth order Bessel beam. As illustrated in FIG. 7, the radius of each annulus may be chosen to be the $J_0$ zeros, so that each annulus spans a single lobe and the gains of each transducer is determined to be the maximum amplitude of the $J_0$ lobe that it spans. In theory such a beam travels to infinity without spreading.

Directional sound beams produced according to the present invention have applications in many products that may benefit from steering sound eg. to alarm a person or animal in a defined area, to transmit audible sound over a long distance with high levels of directivity for military or sports applications, to provide a dynamic (scanning) reproduction system for sound effects and the like etc.

Figure 8:
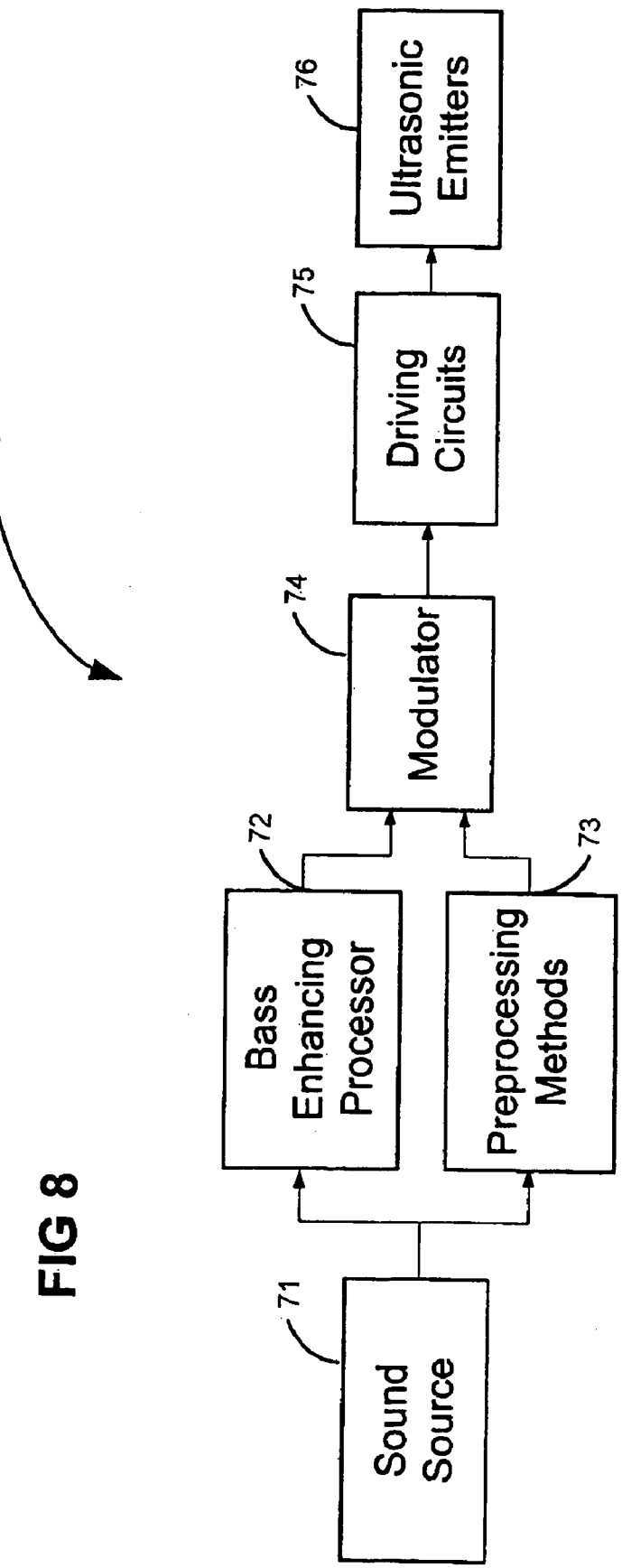
FIG. 8 is a schematic diagram of an ultrasonic system according to an aspect of the present invention.

FIG. 8 is a schematic diagram of an ultrasonic system according to an aspect of the invention. The system, generally identified with numeral 70, commences with sound source 71. Sound source 71 may include any apparatus suitable for generating an audio signal, for example a microphone, optical disc player, magnetic tape player, RF receiver, computer system, etc. Sound source 71 may include internal processing of the signal it generates (e.g. amplification, normalization, bias adjustment, equalization, digital to analog conversion, noise reduction etc.) as is known in the art. Sound source 71 may include a number of components that perform different functions. Moreover, a number of sound sources may be combined to provide the audio signal.

Sound source 71 is coupled to bass enhancing processor 72 and optionally to pre-processor 73. Bass enhancing processor 72, as its name suggests, serves to enhance the signal to provide improved bass perception to the listener. Bass enhancing processor 72 is described in more detail below with reference to FIG. 9. Pre-processor 73 is described in more detail below with reference to FIG. 10. The output from pre-processor 73 and bass enhancing processor 72 are combined and provided to ultrasonic modulator 74.

Ultrasonic modulator 74 generates an ultrasonic carrier wave onto which combined signals from pre-processor 74 and bass enhancing processor 72 are modulated. The ultrasonic carrier wave has a frequency that is above the audible range of human hearing (e.g. at least above 15 kHz, normally above 20 kHz). The frequency of the carrier signal generated by ultrasonic modulator 74 may be any suitable frequency, and is typically selected so that all frequency components of the modulated signal are above 20 kHz. As an example only, a frequency of 40 kHz may be appropriate for use in the system of the present invention.

Also included in system 70 are driving circuit 75 and one or more ultrasonic emitters 76. Driving circuit 75 provides amplification of the modulated signal received from ultrasonic modulator 74, and ultrasonic emitters 76 transmit the modulated signal into the air. Driving circuits 75 and ultrasonic transmitters 76 are conventional in nature, and their particular configurations (power levels, etc.) will depend on the particular application.

Figure 9:
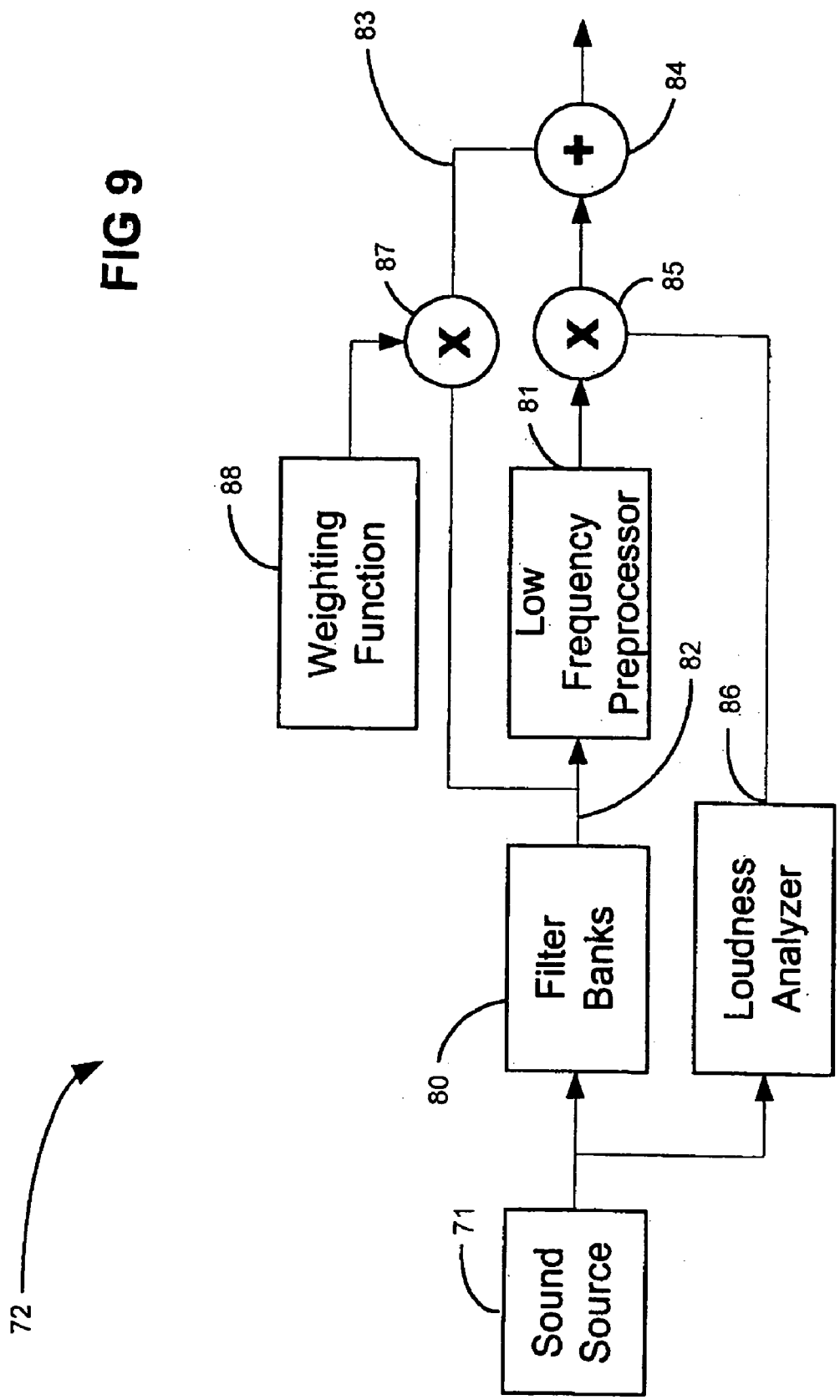
FIG. 9 is a schematic diagram of the bass enhancing module of the system of FIG. 1.

Bass enhancing processor 72 is shown in more detail in FIG. 9. In the exemplary embodiment, the bass enhancing processor includes filter banks 80 and low frequency preprocessor 81. Filter banks 80 separate audio signal received from audio source 71 into two or more frequency bands. In particular, signal 82 in a relatively low frequency band (for example less than 500 Hz) is passed to low frequency preprocessor 81 by providing a low-pass filter in filter banks 80. Filter banks 80 may be provided with other filters to provide other frequency bands.

Low frequency preprocessor 81 includes a harmonics generator that generates harmonics of low frequency signal 82 in a known manner. In particular, the harmonics generator generates a residue harmonic signal having a sequence of harmonics. The sequence of harmonics, generated with respect to each fundamental frequency, contains at least three consecutive harmonics from among the primary set of harmonics for the fundamental frequency.

These harmonics are added to low frequency signal 83 by summer 84. The combined signal is then passed to modulator 74. By adding harmonics of the low frequency signal to the low frequency signal 82, a listener to the signal emitted by ultrasonic emitters 76 will (after demodulation), have improved low frequency perception than is the case without this processing. The signal leaving low frequency preprocessor 81 is passed to amplifier 85.

Also included in the bass enhancing processor 72 is loudness analyzer 86. Loudness analyzer 86 measures the perceived loudness of the fundamental low frequency of sound source 71. According to this measurement, it determines the required amplification/attenuation to apply to the sequence of harmonics generated in low frequency preprocessor 81. This amplification/attenuation is calculated in order to match the loudness of the fundamental frequency and the perceived loudness of the artificially created harmonics. There are well established procedures in the public literature for realizing loudness analyzers. This field is being extensively studied and improved methods are constantly being suggested. Any suitable loudness analyzer may be utilized in the system of the present invention.

Amplifier 87 receives low frequency signal 82 from the filter banks 80, and amplifies the signal based on weighting function 88. Weighting function 88 is a function or a constant that determines the amount of the low frequency signal to be summed to the output of low frequency preprocessor 81. Weighting function 88 is adjusted according to physical bass response efficiency of the unenhanced system itself. For example, if the bass response of the system is poor, the low frequency signal of interest should preferably be filtered out. On the other hand, if the original system exhibits, in a given bass frequency range, an efficiency that approaches its average efficiency, then preferably a full or attenuated intensity of the original low frequency signal of interest is summed with the signal from low frequency preprocessor 81.

After being amplified in amplifiers 85 and 87, the processed signal from low frequency preprocessor 81 and low frequency signal 82 are combined in summer 84. The bass enhanced signals are combined with the output from pre-processor 73 and are passed to modulator 74, and from there to driving circuits 75, and eventually to ultrasonic emitters 76.

Figure 10:
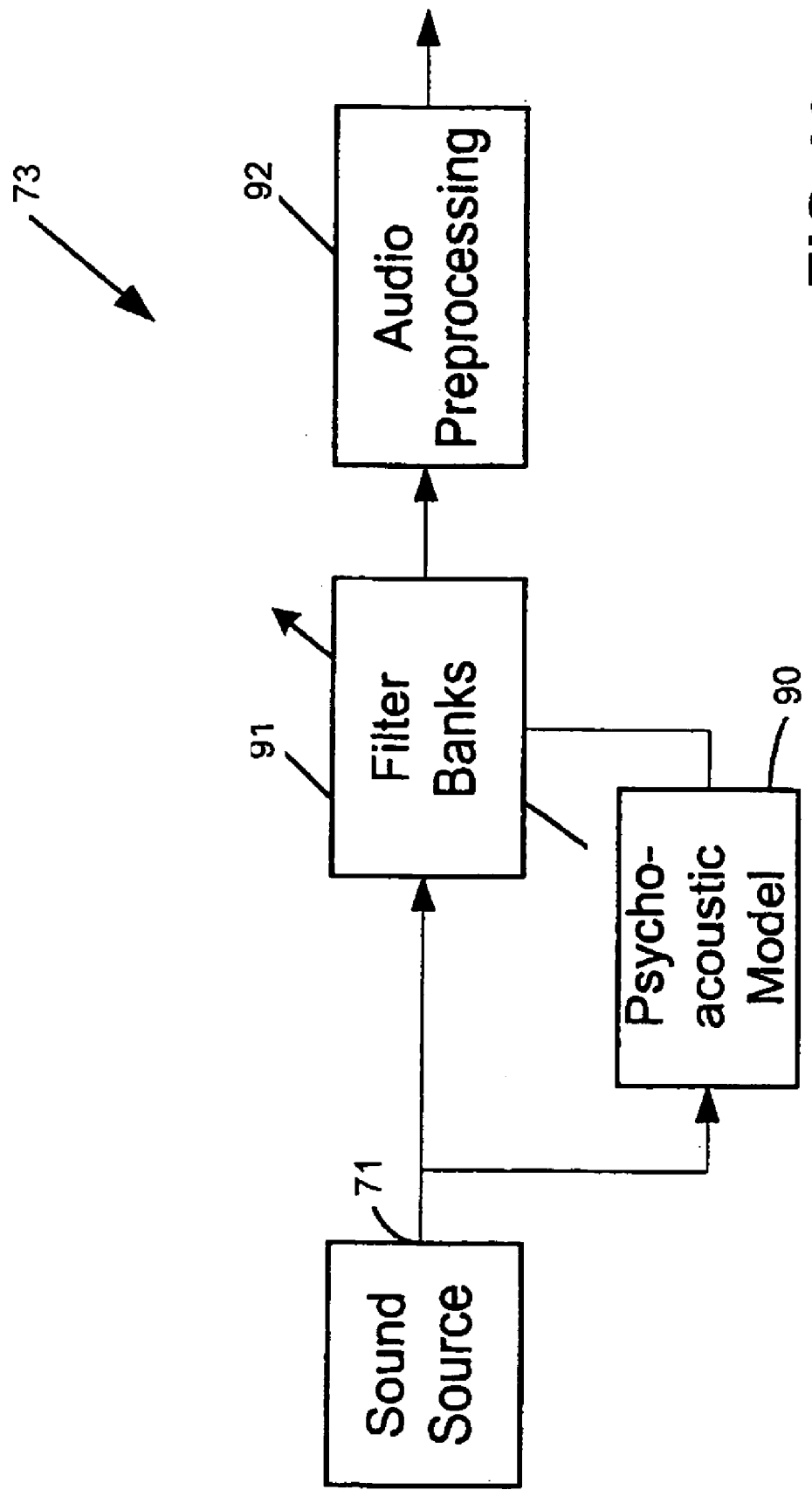
FIG. 10 is a schematic diagram of the preprocessing module of the system of FIG. 1.

FIG. 10 illustrates pre-processor 73 of FIG. 8 in more detail. Preprocessor 73 includes psycho acoustic processor 90, filter banks 91, and audio preprocessor 92. Psycho acoustic processor 90 analyzes the input audio signal and computes the amount of noise masking available as a function of frequency. Processor 90 takes advantage of the human auditory system's inability to hear noise under conditions of auditory masking. This masking is a perceptual property of the human auditory system that occurs whenever the presence of a strong audio signal makes a temporal or spectral neighborhood of weaker audio signals imperceptible. Under such conditions, the frequencies that will not be perceived can be removed/masked from the signal without affecting the perceived quality of the signal.

Filter banks 91 contain a bank of bandpass filters, with overlapping passbands which model the auditory system that is human perception. An approach to modeling the auditory system is to consider the periphery as a fourier transform followed by a number of bandpass filters, and to view the function of entire lower auditory system as being a spectrum estimator. Filter banks 91 are also called the 'auditory filters'. The function of filter banks 91 is to split the signal into plurality of bands, which model the peripheral auditory system. In audio literature, it has been concluded that the ear is primarily a frequency analysis device that can be approximated by bandpass filters, consisting of filters with overlapping frequency bands. There are well-established procedures in the public domain for realizing the filter banks, and accordingly they will not be discussed further here.

Audio preprocessor 92 pre-distorts the signal before sending it to modulator 74. This is typically done to take account of the way in which the ultrasonic signal demodulates in air. One way to pre-distort the signal is to take the square root of the signal, as proposed by Blackstock and described above. Another way to pre-distort the signal is to perform a modified square root method as described below. In this way, after self-demodulation in the air takes place, the resulting distortion of the audio is reduced or minimized.

As can be seen in FIG. 10, the audio signal from sound source 71 is provided to filter banks 91 and psycho acoustic processor 90. After the audio signal passes through filter banks 91, it is processed further in audio preprocessor 92. After leaving audio preprocessor 92, the signal is passed to modulator 74.

Figure 11:
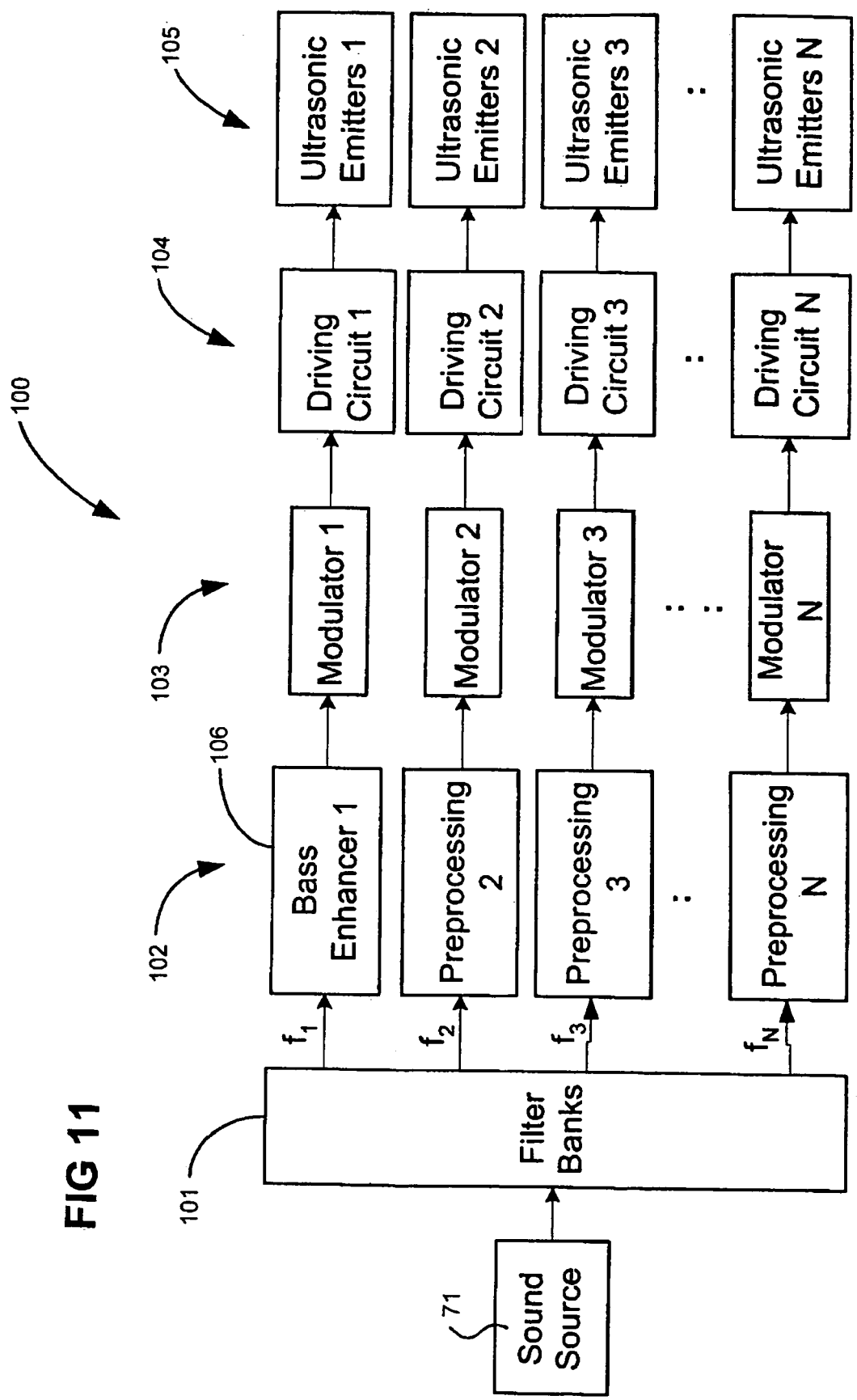
FIG. 11 is a schematic diagram of a pre-modulation multiple path ultrasonic system according to one aspect of the present invention.

FIG. 11 shows a multiple-path ultrasonic system 100 according to one embodiment of the present invention. In this embodiment, the audio signal is split into at least two frequency bands. With this approach, the efficiency of the system may be increased, and the dependency on a particular ultrasonic emitters bandwidth may be reduced. Using this method, ultrasonic emitters can be selected to according to their suitability to transmit a particular band of frequencies. Further, by assigning the different frequency bands to different modulators, it is possible to modulate the signal at different carrier frequencies, which can provide improved matching of modulated signals to different ultrasonic emitters.

As can be seen in FIG. 11, the system 100 includes filter banks 101, a plurality (1–N) of preprocessors 102, a corresponding plurality (1–N) of modulators 103, a corresponding plurality (1–N) of driving circuits 104 and a plurality (1–N) of ultrasonic emitters 105 (or groups of ultrasonic emitters 105). Filter banks 101 include filters having overlapping or non-overlapping frequency pass bands. Typically, the pass bands are centered at frequencies $f_1$ to $f_N$, but the first filter may be a low pass filter and the Nth filter may be a high pass filter. Filter banks 101 divide the signal from sound source 71 into N signals having frequencies centered at the corresponding frequencies $f_1$ to $f_N$ of the filters in the filter band.

Preprocessors 102 preprocess each of the N signals. One processor 106 may be bass enhancing processor 72 of FIG. 8, to enhance a low frequency part of the signal but this is not required. Alternatively, preprocessor 106 may be preprocessor 73 of FIG. 8, or may utilize any other preprocessing method to manipulate signals from filter banks 101. In another embodiment, preprocessor 106 may be provided only for selected frequency bands (e.g. for bass enhancement), or may be omitted entirely.

The plurality of modulators 103 modulate signals received from preprocessors 102 onto ultrasonic carrier waves. Modulators 103 may use the same carrier frequency, but preferably use carrier frequencies that are chosen to correspond to frequency characteristics of the signal $f_N$ or to characteristics of the corresponding ultrasonic emitter 105. Preferably, the frequency of the carrier wave of each modulator 103 is typically matched to the resonant frequency of the corresponding ultrasonic emitter. By way of example only, the signal from sound source 71 may be split into three different frequency bands at 0–600 Hz, 600–4 kHz and 4–16 kHz, which are modulated using carrier frequencies of 40, 50 and 60 kHz respectively. The modulated signals may be transmitted to ultrasonic emitters having resonant frequencies of 40, 50 and 60 kHz respectively. The proposed system may increase the efficiency of the demodulated audio output. In addition, emitters of high power may be selected to transmit the lower frequency signal $f_1$ which may boost the bass of the demodulated audio.

Driving circuits 104 receive modulated signals from modulators 103, amplify them, and provide them to ultrasonic emitters 105.

As mentioned above, 1 to N ultrasonic emitters 105, which receive amplified and modulated signals, are selected to match (as far as possible) characteristics of the 1 to N signals. Preferably, the resonant frequencies of the ultrasonic emitters are selected to be approximately equal to a characteristic frequency of the signal. In particular, the resonant frequency each of the ultrasonic emitters may be matched to the carrier wave frequency provided by the corresponding modulator 103 to which the ultrasonic emitter is coupled, as described above.

Figure 12:
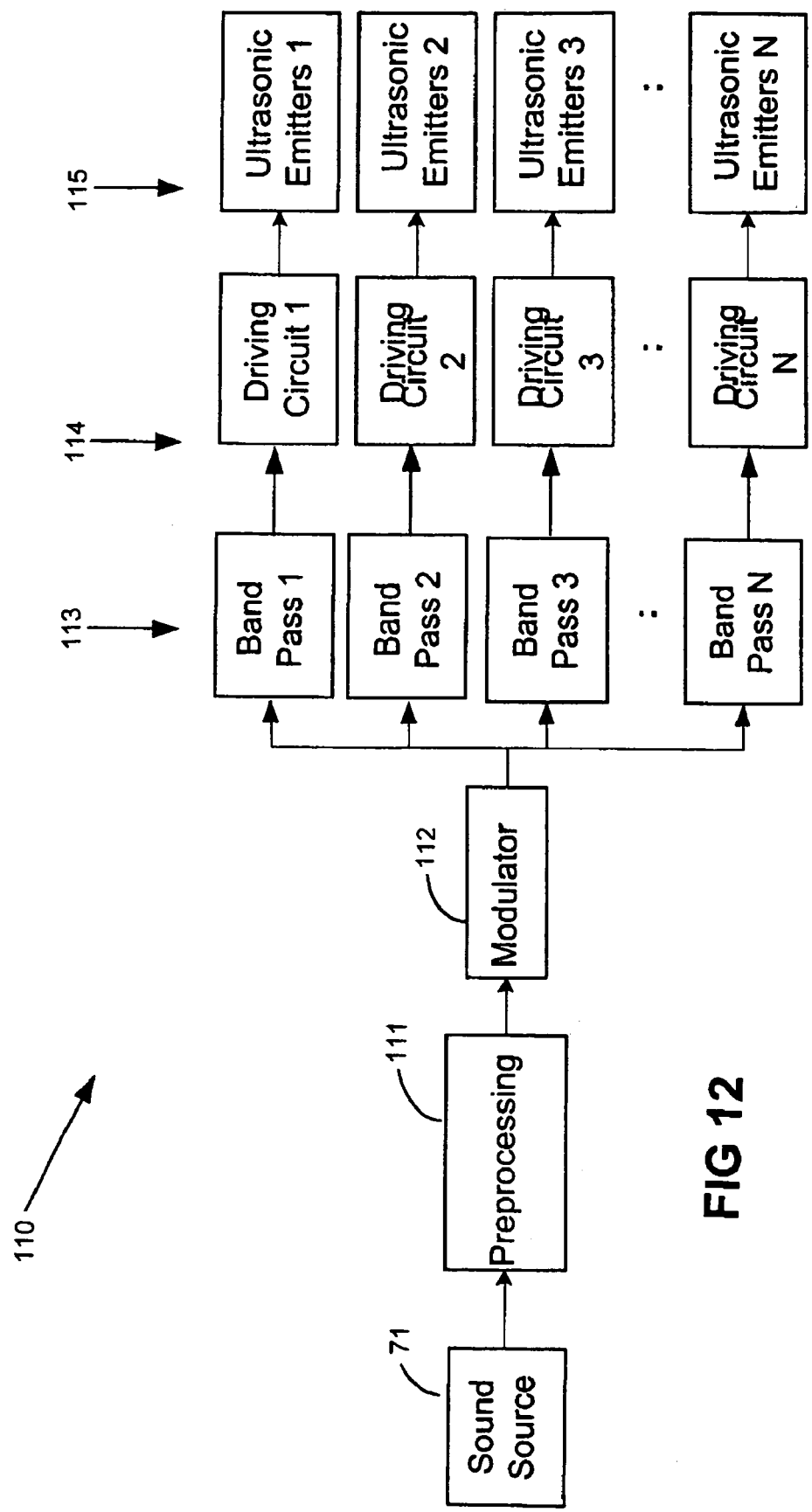
FIG. 12 is a schematic diagram of a post-modulation multiple path ultrasonic system according to one aspect of the present invention.

FIG. 12 shows an alternative multiple-path ultrasonic system 110. As with the embodiment of FIG. 11, the audio signal from audio source 71 is split into at least two frequency bands. In this embodiment however, the signal is split later in the signal path (after modulation) than in the embodiment of FIG. 11. As with the previous embodiment, the embodiment of FIG. 12 provides increased efficiency, and the dependency on a particular ultrasonic emitter's bandwidth will be reduced. Using this method, ultrasonic emitters may be selected according to their suitability to transmit a particular band of frequencies.

As can be seen in FIG. 12, the system 110 includes a preprocessor 111, a modulator 112, a filter bank 113 comprising a plurality of band pass filters (1–N), a corresponding plurality (1–N) of driving circuits 114 and a plurality (1–N) of ultrasonic emitters 115 (or groups of ultrasonic emitters 115).

Preprocessor 111 preprocesses the signal from audio source 71. Preprocessor 111 may utilize any preprocessing method, but it is preferably the preprocessor 72 of FIG. 9.

Modulator 112 modulates the signal received from preprocessor 111 onto an ultrasonic carrier wave, and passes the modulated signal to filter bank 113.

Filter bank 113 includes a number of filters having overlapping or non-overlapping frequency pass bands. Typically, the pass bands are centered at frequencies $f_1$ to $f_N$, but the first filter may be a low pass filter and the Nth filter may be a high pass filter. Filter bank 113 divides the signal from modulator 112 into N signals having frequencies centered at the corresponding frequencies $f_1$ to $f_N$ of the filters in the filter band. Although the signal passed to filter 113 is based on a carrier wave having a characteristic carrier frequency, the signal has different frequency components because the carrier wave has been modulated by the audio signal from the audio source.

For example, if an audio signal with a frequency range of 50–16,000 Hz is modulated onto a carrier wave having a frequency of 40 kHz, the resulting modulated signal will have a frequency range of approximately 24–56 kHz. The filter bank may then, for example, include four filters having frequency bands of 23 to 33 kHz, 31 to 41 kHz, 39 to 49 kHz and 47 to 57 kHz, with the centers of the frequency bands respectively being 28, 36, 44 and 52 kHz, which will cover the entire frequency range the modulated signal.

Driving circuits 114 receive the modulated signals $f_1$ to $f_N$ from the filter bank 113, amplify them, and provide them to ultrasonic emitters 115.

The 1 to N ultrasonic emitters 115 receive the amplified modulated signals from driving circuits 114, and transmit them. Ultrasonic emitters 115 are selected to match (as far as possible) the characteristics of the 1 to N signals. In particular, the resonant frequencies of the ultrasonic emitters are selected to be approximately equal to a characteristic frequency of the signal. In the system of FIG. 12, the resonant frequencies of ultrasonic transmitters 115 are matched to the center frequencies of the corresponding filters in filter bank 113. Therefore, using the four exemplary filters discussed above, the ultrasonic emitters would have resonant frequencies approximately equal to 28, 36, 44 and 52 kHz. Note that in most cases, each ultrasonic emitter 115 is made up of a group of ultrasonic emitters, and the term ultrasonic emitter thus includes both a single ultrasonic emitter as well as a group of ultrasonic transmitters.

Figure 13:
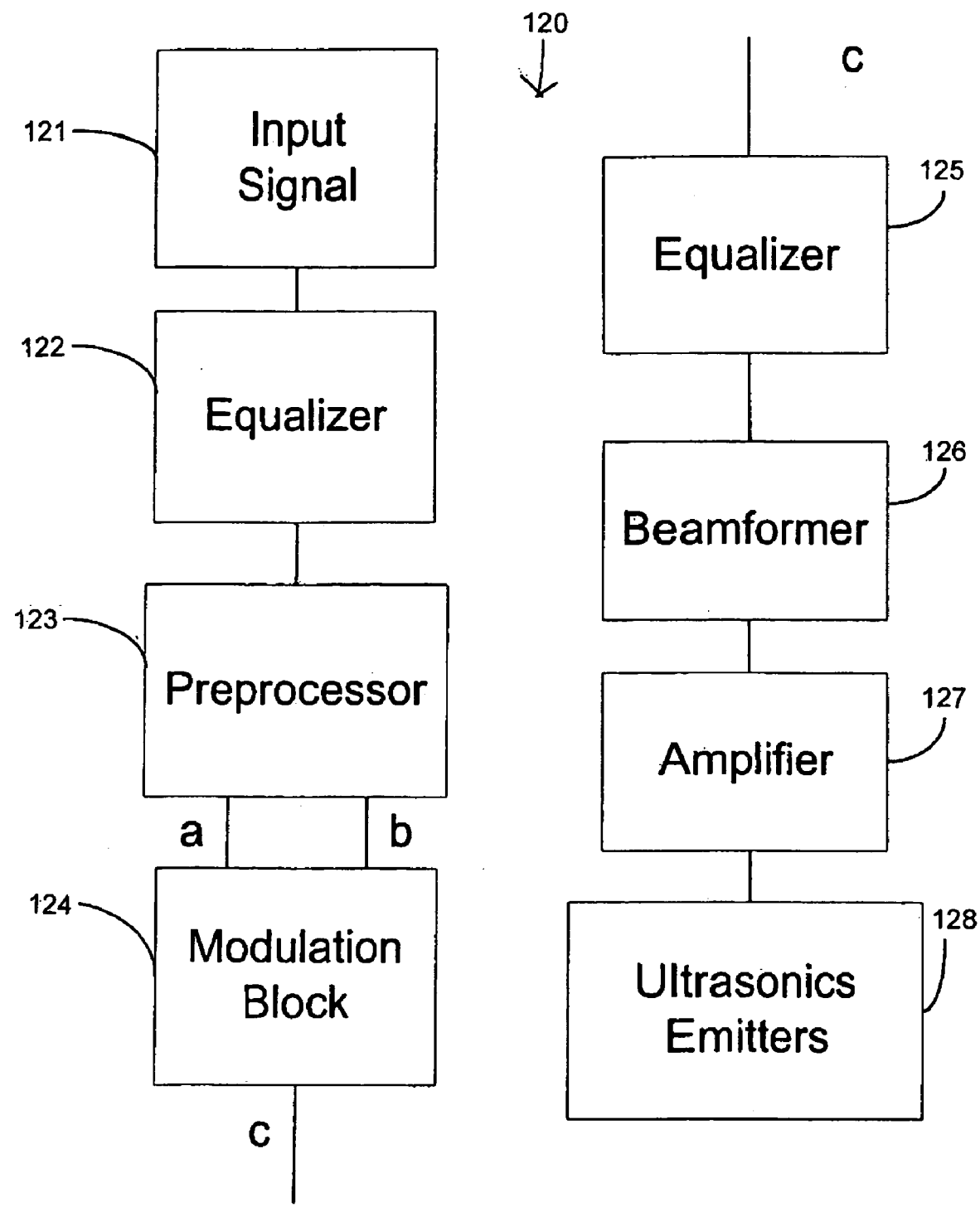
FIG. 13 is a schematic diagram of an ultrasonic signal processing system according to an aspect of the present invention.

FIG. 13 is a schematic diagram that shows an exemplary system according to an aspect of the present invention. The system, generally identified with the numeral 120, commences with sound source 121 that generates an input signal. Sound source 121 may include any apparatus suitable for generating an audio signal, for example a microphone, optical disc player, magnetic tape player, RF receiver, computer system, etc. Sound source 121 may include internal processing of the signal it generates (e.g. amplification, normalization, bias adjustment, equalization, digital to analog conversion, noise reduction etc.) as is known in the art. Also, sound source 121 may itself include a number of components that perform different functions, and a number of sound sources may together combine to provide the signal.

Sound source 121 is coupled to equalizer 122. Equalizer 122 integrates the signal received from sound source 121 twice and then normalizes it so that it occupies an amplitude range of ±1 units. The double integral is performed to correct the second derivative effect of the demodulation process. The normalized signal from equalizer 122 is passed to preprocessor 123, which is described in more detail below with reference to FIG. 14. Preprocessor 123 generates two signals, an "a" signal and a "b" signal, which are passed to modulation block 124. Modulation block 124, which will be described in more detail below with reference to FIG. 17, modulates the two signals onto two ultrasonic carrier waves that are 90° out of phase with each other. This is known as quadrature modulation. The ultrasonic carrier waves used to modulate the "a" and "b" signals have an identical frequency that is above the audible range of the human ear (e.g. above at least 15 kHz, normally above 20 kHz). The frequency of the carrier signals generated by modulation block 122 may be any suitable frequency, and the frequency is typically selected so that all frequency components of the modulated signals are above 20 kHz. As an example only, a frequency of 40 kHz may be appropriate for use in the system of the present invention. After modulation, the two signals "a" and "b" are recombined in modulation block 124, and they are passed to second equalizer 125. Equalizer 125 corrects for distortion that occurs due to bandwidth limitations of the ultrasonic emitters. Equalizer 125 has a transfer function that is an inverse of the transfer function of the ultrasonic emitters. This has the effect of equalizing the overall transfer function, thus increasing overall bandwidth.

After leaving equalizer 125, the signal is passed to beam-former 126. Beam former 126 is application-specific, and modifies the signal to generate necessary signal(s) for beam-forming and beam steering. The particular processing undertaken by beamformer 126 will depend on the particular ultrasonic emitters used, and on the particular directional characteristics required. Such techniques may include techniques described herein as well as techniques known to those of ordinary skill in the art.

Also included in system 120 are amplifier 127 and one or more ultrasonic emitters 128. Amplifier 127 provides amplification of signal(s) received from beamformer 126, and ultrasonic emitters 128 transmit amplified signal(s) into the air. Amplifier 127 and ultrasonic transmitters 128 are conventional in nature, and their particular configurations (power levels, etc.) will depend on the particular application.

Figure 16:
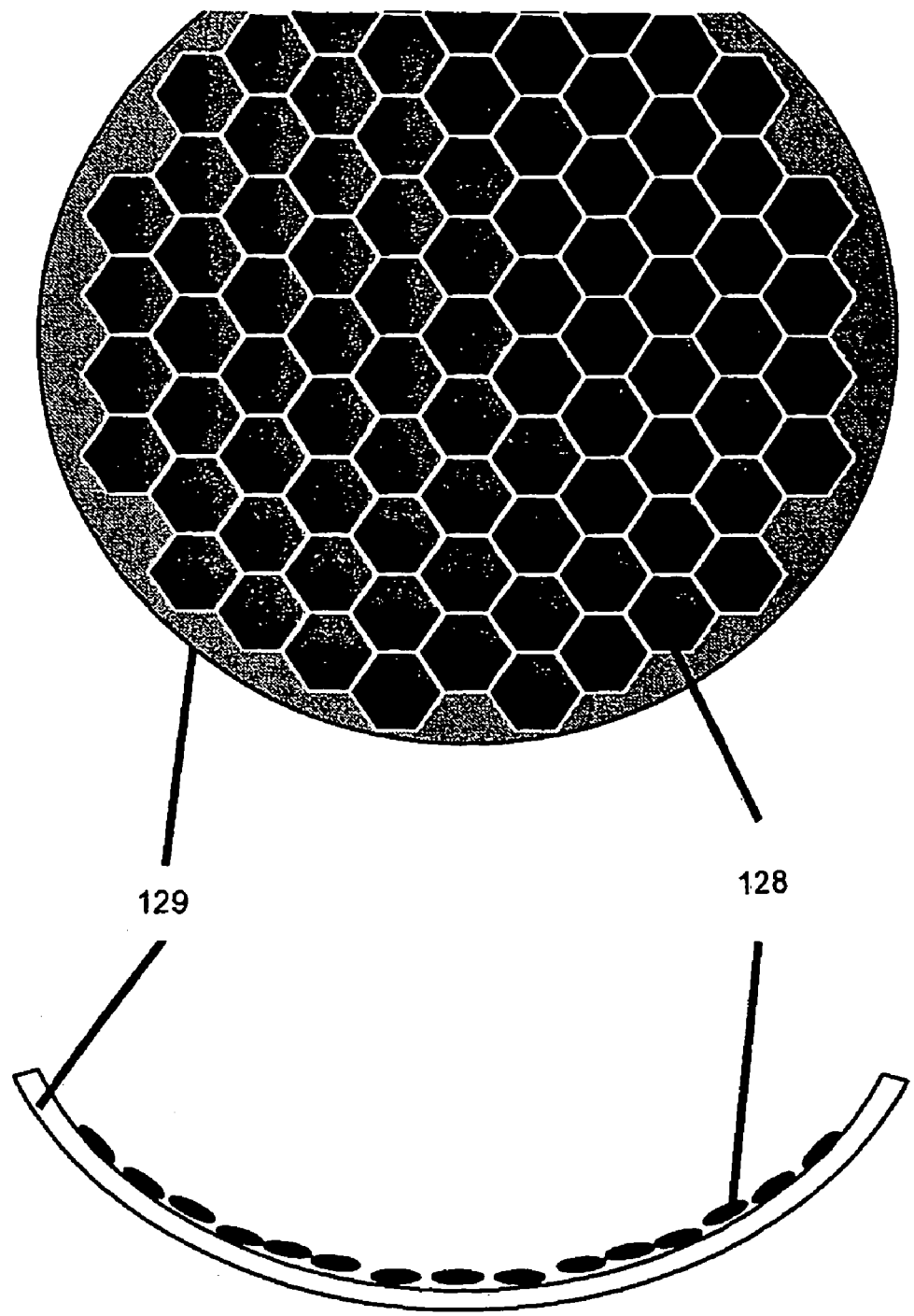
FIG. 16 is a schematic diagram of an ultrasonic emitter suitable for use with the system of FIG. 13.

An exemplary arrangement of ultrasonic emitters is shown in FIG. 16. As can be seen in FIG. 16, a plurality of ultrasonic emitters 128 are mounted adjacent to one another on a shaped backing structure 129. Structure 129 is preferably paraboloid-shaped, which achieves better directivity than a traditional planar array. In addition, the directivity of the ultrasonic wave that is projected from the array can be controlled by adjusting the curvature of the array to achieve different focal points.

Figure 14:
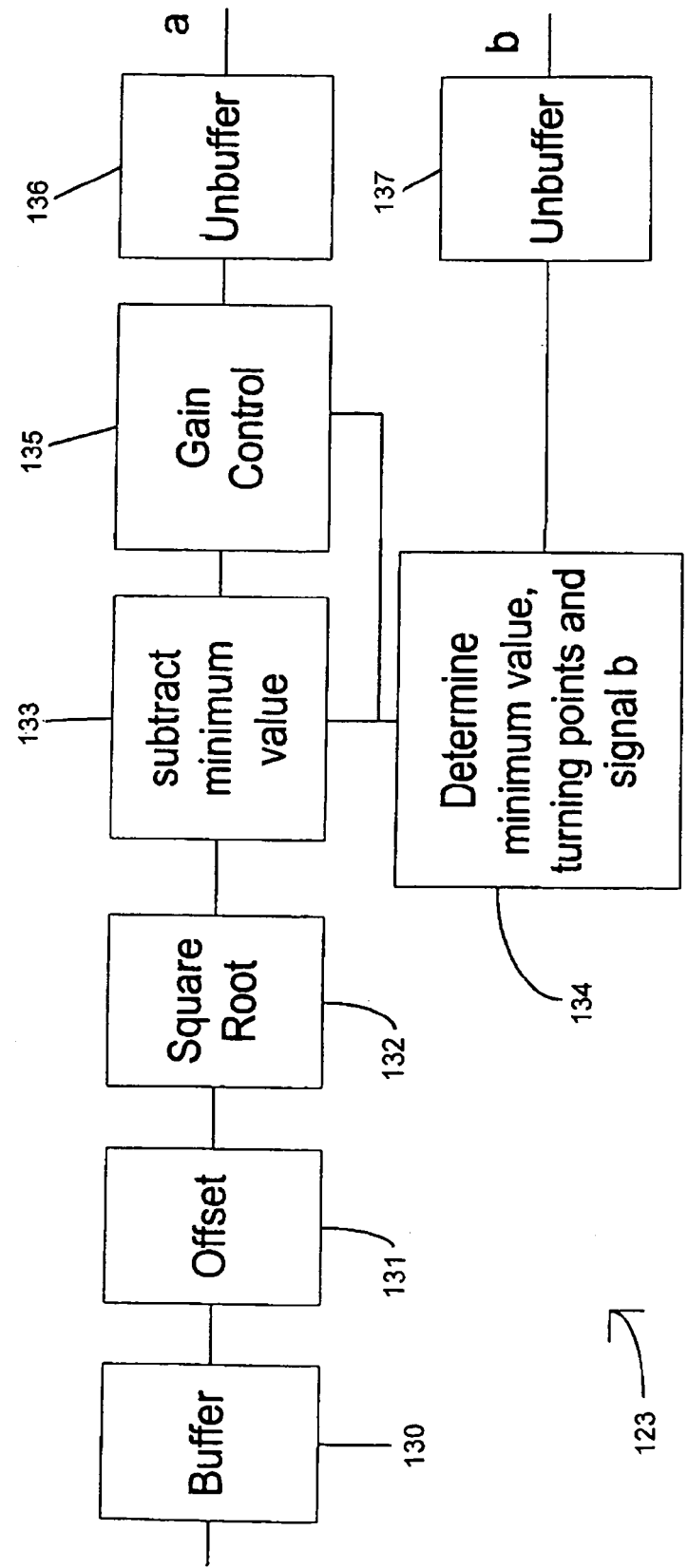
FIG. 14 is a schematic diagram of the preprocessor of the system of FIG. 13.

Preprocessor 123 is shown in more detail in FIG. 14. The signal received from equalizer 122 is first received in buffer 130. Preprocessor 123 processes the audio in a frame-by-frame manner, and buffer 130 generates frames to be processed by repeatedly allowing a selected period of audio to accumulate to form a complete frame, at which time the frame is passed on for further processing to offset generator 131.

Offset generator 131 receives a frame from buffer 130. As mentioned above, the signal has been normalized in equalizer 122 to lie between a maximum value of +1 and a minimum value of −1 and to compensate for the second derivative demodulation effect in air. Offset generator 131 offsets the portion of the signal in the frame by an amount of +1. This may ensure that no part of the signal in the frame is less than zero and that the subsequent square root operation can be performed on the entire frame and the results will all be real values. After performing the offset, offset generator 131 passes the offset signal to square root module 132.

As its name implies, square root module 132 takes the offset signal and performs a square root operation on all values of the offset signal. As mentioned above, the previous offset operation ensures that only real values result from the square root operation. After performing the square root operation, square root module 132 passes the square root signal to subtraction module 133. Subtraction module 133 also passes the signal on to determining module 134.

One function of determining module 134 is to determine the smallest value of the square rooted signal in the frame. If the smallest value of the signal in the frame is within a tolerance (for example a value between 0 to 0.1), this value will be passed to subtraction module 133, otherwise a value of 0 will be passed to subtraction module 133. Passing a value of 0 to subtraction module 133 will have the effect of not modifying the waveform. In subtraction module 133, the received minimum value is subtracted from the entire portion of the signal in the frame, which has the effect of shifting the waveform down for non-zero received values.

When the minimum value is subtracted, the lowest point(s) in the signal in the frame in question may now have a zero value. The shifted signal is then passed both to "flipping point" determining module 134 and to gain control module 135.

Determining module 134 determines where the turning points are in the shifted signal. This determination can be done by identifying where the slope (i.e. the first derivative) of the waveform goes from a negative value (a downslope from left to right) to a positive value (an upslope from left to right). In addition, these turning points should be within a tolerance (for example a value of 0 to 0.1). This can be seen in FIG. 15A, which shows an exemplary signal waveform received from subtraction module 133. In FIG. 15A, selected turning points can be seen at locations A and B, where the slope changes sign from negative to positive within the defined tolerance range. Also, as a result of the subtraction, it can be seen that in FIG. 15A, the signal has a zero value at one location, i.e. at A.

Determining module 134 then alternates gain between +1 and −1 at each selected turning point. This has the effect of "flipping" the portion of the curve between every second set of selected turning points about the zero axis. The effect of this operation on the signal in FIG. 15A can be seen in the signal in FIG. 15B. Before the first selected turning point at A, the gain is set at +1 in this case. Note that the initial gain will always follow the gain of the last portion of the previous frame. The gain of +1 (or −1) is a multiplication factor, not an offset, so that the magnitude at any point on the curve remains unchanged. When determining module 134 identifies a selected turning point at A, the determining module switches the gain to −1. The effect of this is to "flip" or "mirror" the portion of the curve in FIG. 15A between points A and B about the zero axis. The result can be seen on the curve in FIG. 15B between points A and B. When determining module 134 locates the next selected turning point on the curve in FIG. 15A, at point B, the gain is again switched to +1. This results in the portion of the curve in FIG. 15A from point B onwards being identical to the corresponding portion of the curve in FIG. 15B. In the illustrated example, there were only two selected turning points. If there had been additional turning points, the switching of the gain between +1 and −1 would have continued in the same manner at the additional selected turning points.

Determining the turning points and switching of gain is performed by determining module 134. Actual application of gain is performed by gain control module 135. After leaving gain control module 135, the signal in the processed frame now looks, for example, like the curve in FIG. 15A. This signal is passed to unbuffer 136, which is used to reassemble the frames before signal "a" leaves the preprocessor 123. Gain control module 135 also passes its output signal to determining module 134 for use in generating signal "b."

In addition to determining the gain and the selected turning points, determining module 134 also generates signal "b." Signal "b" is used to compensate for the difference in the resulting modulated signal between the ideal square root signal and signal "a." Also, since subsequent frames may have been subtracted by different values to generate signal "a", signal "b" is used to compensate for the discontinuities between frames in signal "a".

Determining module 134 takes the ideal square root signal (which was received from subtraction module 133 to enable determination of the minimum value and the turning points) and subtracts the resulting envelope of signal "a" (for the frame in question) from that of the ideal square root signal. This compensates for the difference between the envelope of the ideal square rooted signal and envelope of signal "a" includes the subtraction of a different minimum value that may have been subtracted in each frame for generating signal "a." This compensation therefore takes into account discontinuities between successive frames. The resulting frame-based signal "b" is passed to unbuffer 137, which functions in the same way as unbuffer 136, and from there to modulation block 124. The resulting envelope of a signal f(t), that is to be modulated by sin $\omega_c t$ (i.e. the modulated signal is f(t)*sin $\omega_c t$), can be easily found by taking the absolute value of f(t) (i.e. |f(t)|).

Figure 17:
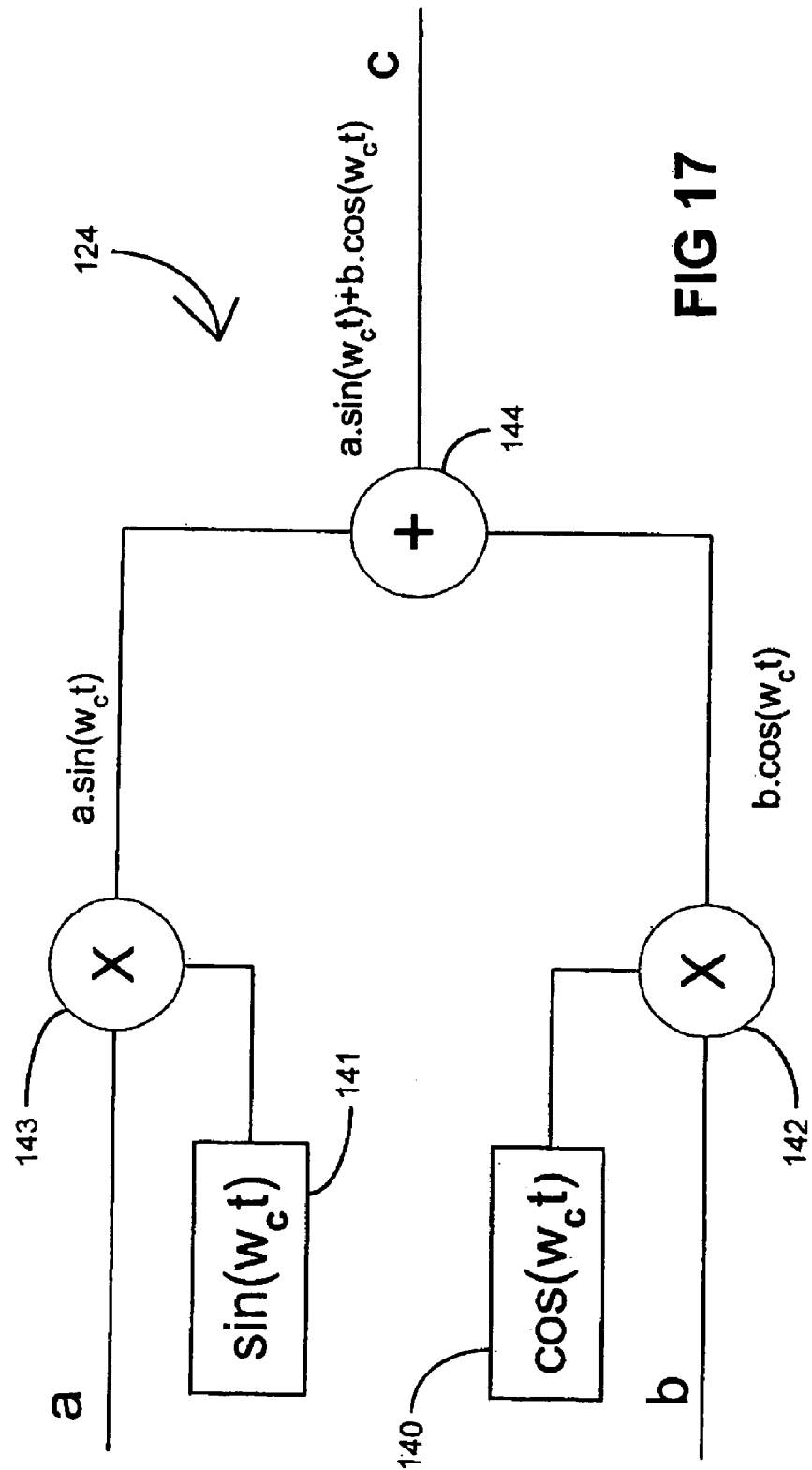
FIG. 17 is a schematic diagram of the modulator of the system of FIG. 13.

Signals "a" and "b" are then passed to the modulation block 124. Modulation block 124 is shown in more detail in FIG. 17, and comprises two ultrasonic carrier wave generators 140, 141, two amplifiers 142, 143, and adder 144. The ultrasonic carrier waves generate sinusoidal, ultrasonic waves onto which signals "a" and "b" are modulated. As can be seen in FIG. 17, generator 140 uses the cosine function of $\omega_c t$ to generate its carrier wave, while generator 143 uses the sine function of $\omega_c t$ to generate its carrier wave. That is, the carrier waves generated by ultrasonic carrier wave generators 140, 141 are orthogonal to one another. It will of course be appreciated that other functions could be used to generate the ultrasonic carrier waves. The ultrasonic carrier waves thus generated are used to control the gain of amplifiers 142 and 143. The signals "a" and "b," which are respectively provided as inputs to amplifiers 143, 142, are thus modulated onto the ultrasonic carrier waves. Modulated signals "a" and "b" are then provided to adder 144, where they are combined to form signal "c." Signal "c" thus is defined by the equation $a \cdot \sin(\omega_c t) + b \cdot \cos(\omega_c t)$.

Signal "c" is provided to equalizer 125 as described above with reference to FIG. 13.

Figure 18:
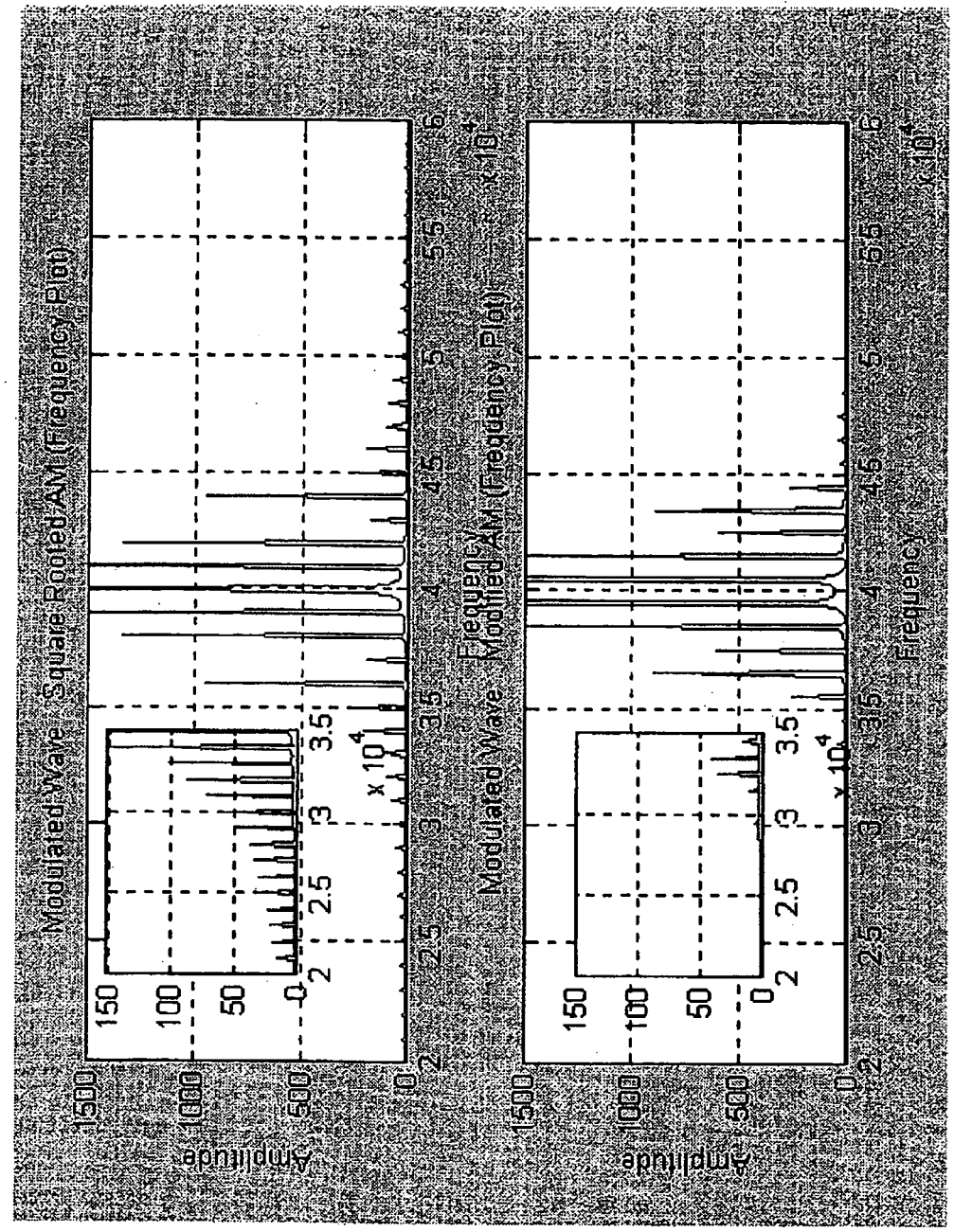
FIG. 18 shows two frequency response graphs comparing the modified square root method of the invention with the traditional square root method.

FIG. 18 shows a comparison between the frequency spectrum of Blackstock's square rooted and modulated waveform and the modified square rooted and modulated waveform. In FIG. 18, the audio signal is a combination of 1 kHz, 2 kHz and 4 kHz sinusoidal waves, while the ultrasonic carrier wave has a frequency of 40 kHz. As can be seen in FIG. 18, the traditional square root method (upper graph) yields many harmonics, while the modified square root method of the present invention (lower graph) does not. This has the advantage of reducing the bandwidth required of the ultrasonic emitters.

Figure 19:
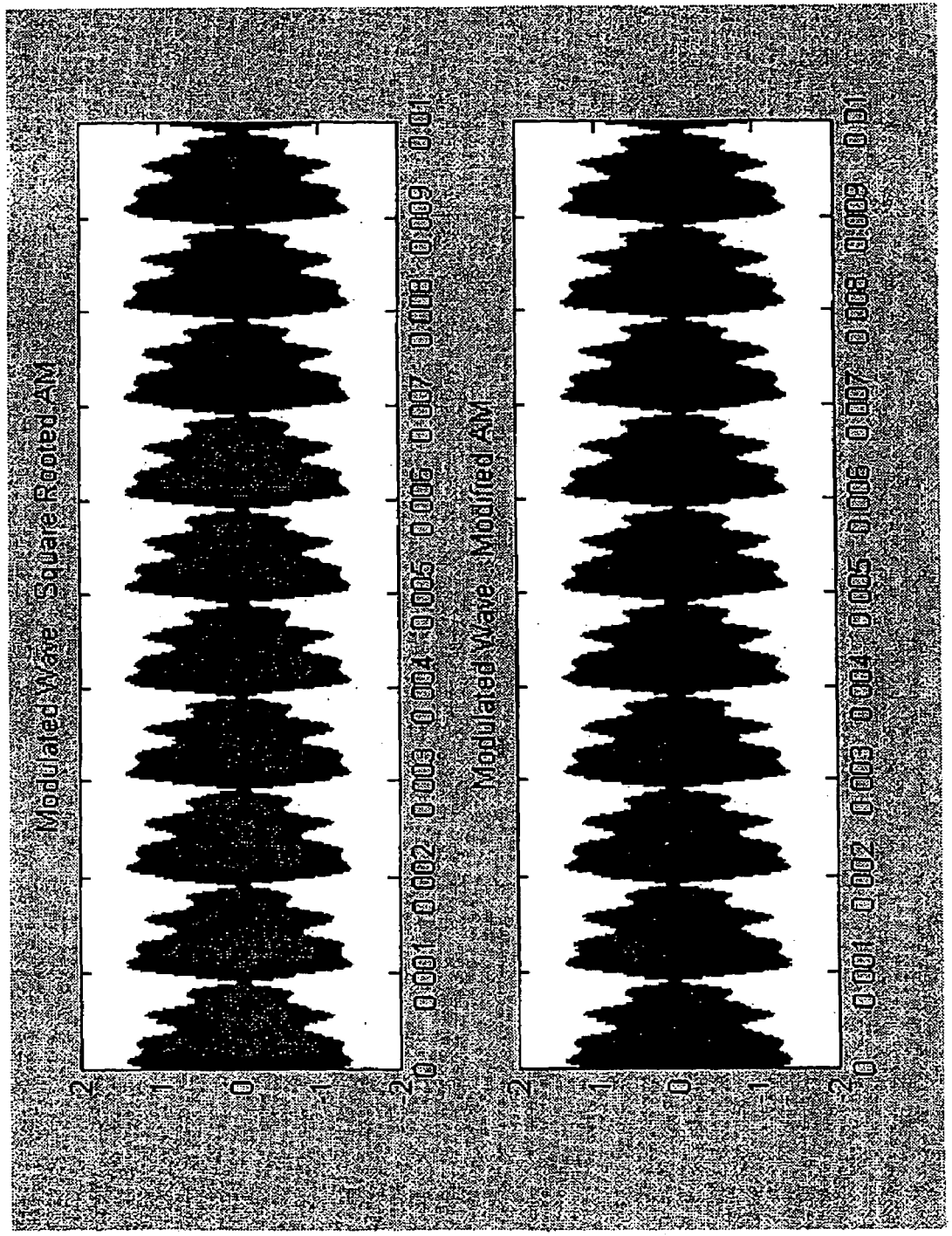
FIG. 19 shows two modulated waveform graphs comparing the modified square root of the invention with the traditional square root method for a 1 kHz, 2 kHz and 4 kHz modulating waveform.

FIG. 19 shows the actual modulated signal (multi-tone signal of 1 kHz, 2 kHz and 4 kHz modulated onto a 40 kHz carrier wave) for the traditional square root method (upper graph) and the modified square root method of the present invention (lower graph). As can be seen in FIG. 19, there is little no difference between the envelope of the modulated signals provided to the ultrasonic emitters.

While the present invention has been described in terms of several embodiments, it is to be understood that various alterations, modifications and/or permutations thereof may become apparent to those skilled in the art upon a reading of the specification and study of the drawings and may be introduced into the constructions and arrangements of parts previously described without departing from the spirit or ambit of the present invention.

The invention claimed is:

1. Method for steering a directional audio beam that is self-demodulated from an ultrasound carrier, said method including the steps of:
generating an audio signal;
generating an ultrasound carrier signal;

modulating said carrier signal with said audio signal;

adjusting both amplitude and phase of said audio signal and said carrier signal to steer said audio beam to a desired direction, wherein the amplitude and phase of said audio signal is adjusted in a first amplitude and phase adjustment module and the amplitude and phase of said carrier signal is adjusted in a second amplitude and phase adjustment module; and combining outputs of said first and second amplitude and phase adjustment modules to generate an ultrasound beam driven in said direction by said modulated carrier signal.

2. The method according to claim 1 including suppressing a sidelobe of the ultrasound beam.

3. The method according to claim 1 including weighting said audio and/or carrier signal by a zeroth order Bessel function to synthesize a Bessel distribution source.

4. Method according to claim 3 wherein said step of generating an ultrasound beam includes driving a plurality of ultrasound transducer elements with said modulated carrier signal and said step of weighting includes adjusting gain and delay of said audio and/or carrier signal prior to driving each transducer element.

5. Method according to claim 1 wherein said step of generating an ultrasound beam includes driving a plurality of ultrasound transducer elements via a corresponding plurality of matching filters adapted to adjust the phase of the modulated carrier signal to the resonant frequency of the associated transducer element.

6. Method according to claim 1 including detecting the location of a potential listener and steering said audio beam towards said location.

7. Method according to claim 1 including reflecting said audio beam from an intermediate surface comprising a billboard panel.

8. A method of processing an audio signal, including:
performing a square root operation on the audio signal to generate a square rooted signal;

alternating the gain of the square rooted signal between positive and negative gain values at selected locations to generate a flipped signal, wherein the selected locations of the signal are minimum turning points of the signal;

modulating the flipped signal onto a first ultrasonic carrier wave; and offsetting the audio signal by a predetermined amount prior to performing square root operation to ensure that the square root operation only results in real values.

9. The method of claim 8 further including the step of:
dividing the audio signal into a plurality of frames;
determining, after the offsetting step;
a minimum value of a portion of the audio signal in a particular frame;
subtracting the minimum value from the portion of the audio signal in the particular frame; and
compensating the flipped signal in adjacent frames for discontinuities resulting from subtracting different minimum amounts in adjacent frames.

10. The method of claim 8 further including the steps of:
determining a first modulation envelope for the processed audio signal;
determining a second modulation envelope for an ideal square rooted s determining the difference between the first and second modulation envelopes; and
modulating the difference between the first and second modulation envelopes onto a second ultrasonic carrier wave.

11. Method according to claim 6 wherein said step of generating an ultrasound beam is performed by means of a plurality of transducer elements and the id step of steering said audio beam is performed by means of a stepper motor for rotating said transducer elements relative to at least one axis.

* * * * *

UNITED STATES PATENT AND TRADEMARK OFFICE
CERTIFICATE OF CORRECTION

| | | |
|---|---|---|
| PATENT NO. | : 7,146,011 B2 | |
| APPLICATION NO. | : 10/789243 | |
| DATED | : December 5, 2006 | |
| INVENTOR(S) | : Jun Yang et al. | |

It is certified that error appears in the above-identified patent and that said Letters Patent is hereby corrected as shown below:

Column 20, line 22, delete claim 10 in its entirety, and substitute the following in its place:

-- 10.  The method of claim 8 further including the steps of:
determining a first modulation envelope for the processed audio signal;
determining a second modulation envelope for an ideal square rooted signal;
determining the difference between the first and second modulation envelopes; and
modulating the difference between the first and second modulation envelope onto a second ultrasonic carrier wave. --

Column 20, line 33, delete "id."

Signed and Sealed this

Sixth Day of March, 2007

JON W. DUDAS
*Director of the United States Patent and Trademark Office*